United States Patent
Boschelli et al.

[11] Patent Number: 5,990,146
[45] Date of Patent: Nov. 23, 1999

[54] BENZIMIDAZOLES FOR INHIBITING PROTEIN TYROSINE KINASE MEDIATED CELLULAR PROLIFERATION

[75] Inventors: Diane Harris Boschelli, New City, N.Y.; William Alexander Denny, Pakuranga, New Zealand; Annette Marian Doherty, Paris, France; James Marino Hamby, Ann Arbor, Mich.; Sonya Shah Khatana, Leawood, Kans.; James Bernard Kramer, Sylvania, Ohio; Brian Desmond Palmer, Glendene, New Zealand; Howard Daniel Hollis Showalter, Ann Arbor, Mich.

[73] Assignee: Warner-Lambert Company, Morris Plains, N.J.

[21] Appl. No.: 09/135,470

[22] Filed: Aug. 17, 1998

Related U.S. Application Data

[60] Provisional application No. 60/056,609, Aug. 20, 1997.

[51] Int. Cl.$^6$ .................. A61K 31/415; C07D 235/08
[52] U.S. Cl. .................. 514/394; 514/393; 548/302.1; 548/304.4; 548/304.7
[58] Field of Search .................. 548/302.1, 304.4, 548/304.7; 514/393, 394

[56] References Cited

U.S. PATENT DOCUMENTS

| | | | |
|---|---|---|---|
| 3,644,382 | 2/1972 | Clemence et al. | 260/295 F |
| 4,186,135 | 1/1980 | Thominet et al. | 260/326.34 |
| 4,492,708 | 1/1985 | Spitzer | 424/273 AB |
| 5,283,242 | 2/1994 | Ellingboe | 514/186 |
| 5,360,809 | 11/1994 | Axelsson et al. | 514/338 |
| 5,527,548 | 6/1996 | Tyortyalian | 426/72 |
| 5,552,426 | 9/1996 | Lunn et al. | 514/394 |
| 5,554,632 | 9/1996 | Teuber et al. | 514/338 |

FOREIGN PATENT DOCUMENTS

| | | |
|---|---|---|
| 0563001A1 | 9/1993 | European Pat. Off. . |
| 0616807A1 | 9/1994 | European Pat. Off. . |
| 96/40644 | 12/1996 | WIPO . |
| 96/40645 | 12/1996 | WIPO . |

*Primary Examiner*—Laura L. Stockton
*Attorney, Agent, or Firm*—Todd M. Crissey

[57] ABSTRACT

Benzimidazoles of Formula I below are inhibitors of protein tyrosine kinases, and are useful in treating cellular proliferation.

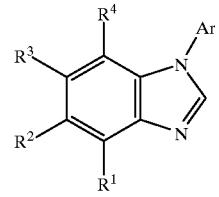

I

The compounds are especially useful in treating cancer, atherosclerosis, restenosis, and psoriasis.

9 Claims, No Drawings

BENZIMIDAZOLES FOR INHIBITING PROTEIN TYROSINE KINASE MEDIATED CELLULAR PROLIFERATION

CROSS REFERENCES TO RELATED APPLICATIONS

This application claims priority of U.S. Ser. No. 60/056,609, filed Aug. 20, 1997.

FIELD OF THE INVENTION

This invention relates to the inhibition of protein tyrosine kinase (PTK) mediated cellular proliferation. More specifically, this invention relates to benzimidazoles and their use in inhibiting cellular proliferation and protein tyrosine kinase enzymatic activity.

BACKGROUND OF THE INVENTION

Many disease states are characterized by the uncontrolled proliferation and differentiation of cells. These disease states encompass a variety of cell types and maladies such as cancer, atherosclerosis, restenosis, and psoriasis. Growth factor stimulation, autophosphorylation, and the phosphorylation of intracellular protein substrates are important biological events in the pathomechanisms of proliferative diseases.

In normal cells, the phosphorylation of tyrosine residues on protein substrates serves a critical function in intracellular growth signaling pathways initiated by stimulated extracellular growth factor receptors. For example, the association of growth factors such as Platelet Derived Growth Factor (PDGF), Fibroblast Growth Factor (FGF), and Epidermal Growth Factor (EGF) with their respective extracellular receptors, PDGFr, FGFr, and EGFr, activates intracellular tyrosine kinase enzyme domains of these receptors, thereby catalyzing the phosphorylation of either intracellular substrates or the receptors themselves. The phosphorylation of growth factor receptors in response to ligand binding is known as autophosphorylation.

For example, the EGF receptor has as its two most important ligands EGF and Transforming Growth Factor α, (TGFα). The receptors appear to have only minor functions in normal adult humans, but are implicated in the disease processes of a large portion of all cancers, especially colon and breast cancer. The closely related Erb-B2 and Erb-B3 receptors have a family of Heregulins as their major ligands, and receptor overexpression and mutation have been unequivocally demonstrated as the major risk factor in poor prognosis breast cancer.

The proliferation and directed migration of vascular smooth muscle cells (VSMC) are important components in such processes as vascular remodeling, restenosis and atherosclerosis. Platelet-derived growth factor has been identified as one of the most potent endogenous VSMC mitogens and chemoattractants. Elevated vascular mRNA expression of PDGF-A and -B chains and PDGF receptors has been observed in balloon-injured rat carotid arteries (*J Cell. Biol.*, 1990; 111: 2149–2158). In this injury model, infusion of PDGF also greatly increases intimal thickening and migration of VSMC (*J. Clin. Invest.*, 1992; 89: 507–511). Furthermore, PDGF-neutralizing antibodies significantly reduce intimal thickening following balloon injury (*Science*, 1991; 253: 1129–1132). Tyrphostin receptor tyrosine kinase inhibitors which block the PDGF signal transduction pathway have been shown to inhibit PDGF stimulated receptor tyrosine kinase phosphorylation in vivo in the rat cuff injury model (*Drug Develop. Res.*, 1993; 29: 158–166).

Both acidic fibroblast growth factor (aFGF) and basic fibroblast growth factor (bFGF) have many biological activities, including the ability to promote cellular proliferation and differentiation. Direct evidence in support of FGF involvement in VSMC has been reported by Lindner and Reidy (*Proc. Natl. Acad. Sci USA,* 1991; 88: 3739–3743), who demonstrated that the systemic injection of a neutralizing antibody against bFGF prior to balloon angioplasty of rat carotid arteries inhibited injury-induced medial SMC proliferation by greater than 80% when measured 2 days after injury. It is likely that bFGF released from damaged cells is acting in a paracrine manner to induce VSMC growth. Recently, Lindner and Reidy (*Cir. Res.,* 1993; 73: 589–595) demonstrated an increased expression of both MRNA for bFGF and FGFR-1 in replicating VSMCs and endothelium in en face preparations of balloon-injured rat carotid arteries. The data provides evidence that in injured arteries the ligand/receptor system of bFGF and FGFR-1 may be involved in the continued proliferative response of VSMCs leading to neointima formation.

Buchdunger, et al., *Proc. Natl. Acad. Sci.*, Vol. 92, March 1995, 2558–2562, reported the inhibition of the PDGF signal transduction pathway both in vitro and in vivo by a PDGF receptor tyrosine protein kinase inhibitor. The compound showed antitumor activity in tumor models using astrocytoma cell lines.

Thus, EGF, PDGF, FGF, and other growth factors play pivotal roles in the pathomechanisms of cellular proliferative diseases such as cancer, atherosclerosis, and restenosis. Upon association with their respective receptors, these growth factors stimulate tyrosine kinase activity as one of the initial biochemical events leading to DNA synthesis and cell division. It thereby follows that compounds which inhibit protein tyrosine kinases associated with intracellular growth factor signal transduction pathways are useful agents for the treatment of cellular proliferative diseases. We have now discovered that certain benzimidazoles inhibit protein tyrosine kinases, and are useful in treating and preventing atherosclerosis, restenosis, and cancer.

SUMMARY OF THE INVENTION

The present invention provides a method of treating cancer, the method comprising administering to a patient having cancer a therapeutically effective amount of a compound of Formula I

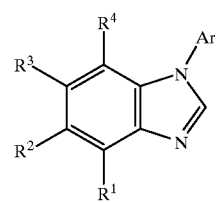

wherein

Ar is aryl, substituted aryl, heteroaryl, or substituted heteroaryl;

$R^1$, $R^2$, $R^3$, and $R^4$ are each independently hydrogen, $C_1$–$C_6$ alkyl, —$OC_1$–$C_6$ alkyl, —OH, halogen, —$CO_2R^a$, —$CONR^aR^b$, —$NO_2$, —$NR^aR^b$, —$COC_1$–$C_6$ alkyl, —CHO, —CN, —$SO_2C_1$–$C_6$ alkyl,

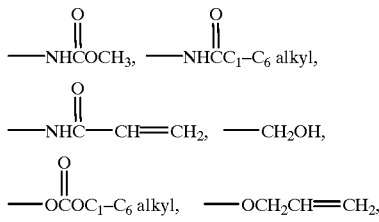

—OCH$_2$CH(OH)CH$_2$OH, —O(CH$_2$)$_n$NR$^a$R$^b$, —O(CH$_2$)$_n$-morpholino, —SH, —SC$_1$–C$_6$ alkyl, or —S(CH$_2$)$_n$NR$^a$R$^a$, or R$^2$ and R$^3$ together can form a cycloalkyl ring that may contain one or more heteroatom;

R$^a$ and R$^b$ are each independently hydrogen or C$_1$–C$_6$ alkyl, n is 0 to 5, and the pharmaceutically acceptable salts, esters, amides, and prodrugs thereof.

The present invention also provides a method of treating or preventing restenosis, the method comprising administering to a patient having restenosis or at risk of having restenosis a therapeutically effective amount of a compound of Formula I

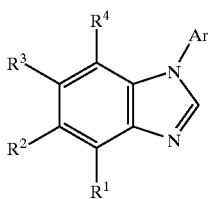

I wherein

Ar is aryl, substituted aryl, heteroaryl, or substituted heteroaryl;

R$^1$, R$^2$, R$^3$, and R$^4$ are each independently hydrogen, C$_1$–C$_6$ alkyl, —OC$_1$–C$_6$ alkyl, —OH, halogen, —CO$_2$R$^a$, —CONR$^a$R$^b$, —NO$_2$, —NR$^a$R$^b$, —COC$_1$–C$_6$ alkyl, —CHO, —CN, —SO$_2$C$_1$–C$_6$ alkyl,

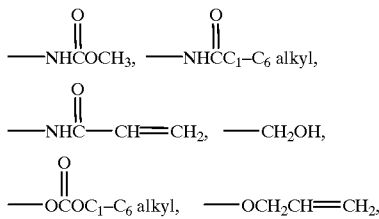

—OCH$_2$CH(OH)CH$_2$OH, —O(CH$_2$)$_n$NR$^a$R$^b$, —O(CH$_2$)$_n$ N-morpholino, —SH, —SC$_1$–C$_6$ alkyl, or —S(CH$_2$)$_n$ NR$^a$R$^b$, or R$^2$ and R$^3$ together can form a cycloalkyl ring that may contain one or more heteroatom;

R$^a$ and R$^b$ are each independently hydrogen or C$_1$–C$_6$ alkyl, n is 0 to 5, and the pharmaceutically acceptable salts, esters, amides, and prodrugs thereof.

In another embodiment, the present invention provides a method of treating atherosclerosis, the method comprising administering to a patient having atherosclerosis a therapeutically effective amount of a compound of Formula I

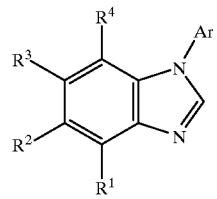

I wherein

Ar is aryl, substituted aryl, heteroaryl, or substituted heteroaryl;

R$^1$, R$^2$, R$^3$, and R$^4$ are each independently hydrogen, C$_1$–C$_6$ alkyl, -OC$_1$–C$_6$ alkyl, —OH, halogen, —CO$_2$R$^a$, —CONR$^a$R$^b$, —NO$_2$, —NR$^a$R$^b$, —COC$_1$–C$_6$ alkyl, —CHO, —CN, —SO$_2$C$_1$–C$_6$ alkyl,

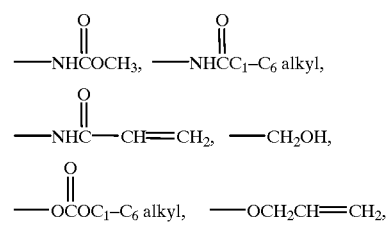

—OCH$_2$CH(OH)CH$_2$OH, —O(CH$_2$)$_n$NR$^a$R$^b$, or —O(CH$_2$)$_n$N-morpholino, —SH, —SC$_1$–C$_6$ alkyl, or —S(CH$_2$)$_n$NR$^a$R$^a$, or R$^2$ and R$^3$ together can form a cycloalkyl ring that may contain one or more heteroatom;

R$^a$ and R$^b$ are each independently hydrogen or C$_1$–C$_6$ alkyl, n is 0 to 5, and the pharmaceutically acceptable salts, esters, amides, and prodrugs thereof.

Also provided is a method of treating psoriasis, the method comprising administering to a patient having psoriasis a therapeutically effective amount of a compound of Formula I

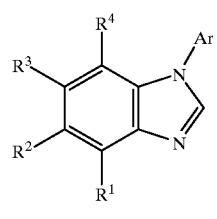

I wherein

Ar is aryl, substituted aryl, heteroaryl, or substituted heteroaryl;

R$^1$, R$^2$, R$^3$, and R$^4$ are each independently hydrogen, C$_1$–C$_6$ alkyl, —OC$_1$–C$_6$ alkyl, —OH, halogen, —CO$_2$R$^a$, —CONR$^a$R$^b$, —NO$_2$, —NR$^a$R$^b$, —COC$_1$–C$_6$ alkyl, —CHO, —CN, —SO$_2$C$_1$–C$_6$ alkyl,

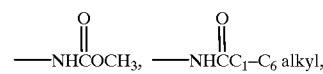

-continued

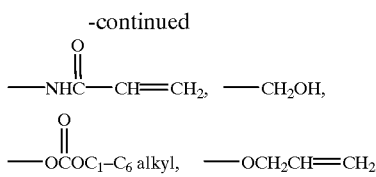

—OCH$_2$CH(OH)CH$_2$OH, —O(CH$_2$)$_n$NR$^a$R$^b$, —O(CH$_2$)$_n$ N-morpholino, —SH, —SC$_1$–C$_6$ alkyl, or —S(CH$_2$)$_n$ NR$^a$R$^b$, or R$^2$ and R$^3$ together can form a cycloalkyl ring that may contain one or more heteroatom;

R$^a$ and R$^b$ are each independently hydrogen or C$_1$–C$_6$ alkyl, n is 0 to 5, and the pharmaceutically acceptable salts, esters, amides, and prodrugs thereof.

In addition, the present invention provides a method of inhibiting protein tyrosine kinases, the method comprising administering to a patient in need of protein tyrosine kinases inhibition a protein tyrosine kinase inhibiting amount of a compound of Formula I

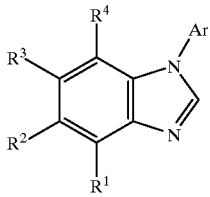

I wherein

Ar is aryl, substituted aryl, heteroaryl, or substituted heteroaryl;

R$^1$, R$^2$, R$^3$, and R$^4$ are each independently hydrogen, C$_1$–C$_6$ alkyl, —OC$_1$–C$_6$ alkyl, —OH, halogen, —CO$_2$R$^a$, —CONR$^a$R$^b$, —NO$_2$, —NR$^a$R$^b$, —COC$_1$–C$_6$ alkyl, —CHO, —CN, —SO$_2$C$_1$–C$_6$ alkyl, —NHCOCH$_3$,   —NHCC$_1$–C$_6$ alkyl,

—NHC—CH=CH$_2$,   —CH$_2$OH,

—OCOC$_1$–C$_6$ alkyl,   —OCH$_2$CH=CH$_2$,

—OCH$_2$CH(OH)CH$_2$OH, —O(CH$_2$)$_n$NR$^a$R$^b$, —O(CH$_2$)$_n$ N-morpholino, —SH, —SC$_1$–C$_6$ alkyl, or —S(CH$_2$)$_n$ NR$^a$R$^b$, or R$^2$ and R$^3$ together can form a cycloalkyl ring that may contain one or more heteroatom;

R$^a$ and R$^b$ are each independently hydrogen or C$_1$–C$_6$ alkyl, n is 0 to 5, and the pharmaceutically acceptable salts, esters, amides, and prodrugs thereof In a preferred embodiment, the protein tyrosine kinase is SRC. In another preferred embodiment, the protein tyrosine kinase is EGFr. In another preferred embodiment, the protein tyrosine kinase is FGFr. In still another preferred embodiment, the protein tyrosine kinase is PDGFr.

The present invention also provides the compounds:
1-(3-Hydroxyphenyl)benzimidazole;
1-(3-Aminophenyl)benzimidazole;
1-(3-Formylphenyl)benzimidazole;
1-(4-Carbomethoxyphenyl)benzimidazole;
4-Hydroxy-1-phenylbenzimidazole;
5-Methyl-1-phenylbenzimidazole;
1-Phenylbenzimidazole-5-carboxylic acid;
Methyl 1-Phenylbenzimidazole-5-carboxylate;
1-Phenylbenzimidazole-5-carboxamide;
5-Acetyl-1-phenylbenzimidazole;
1-Phenylbenzimidazole-5-carboxaldehyde;
1-Phenylimidazo-1H-imidazo[4,5-c]pyridine;
5-Acetamido-1-phenylbenzimidazole;
5-Propionamido-1-phenylbenzimidazole;
5-Acrylamido-1-phenylbenzimidazole;
5-(Hydroxymethyl)-1-phenylbenzimidazole;
5-Ethoxy-1-phenylbenzimidazole;
1-Phenyl-5-propoxybenzimidazole;
5-Isopropoxy-1-phenylbenzimidazole;
5-Butoxy-1-phenylbenzimidazole
5-Allyloxy-1-phenylbenzimidazole;
5-(2,3-Dihydroxypropoxy)-1-phenylbenzimidazole;
5-(2,3-Epoxypropoxy)-1-phenylbenzimidazole;
5-(2-Aminoethoxy)-1-phenylbenzimidazole;
5-[2-(N,N-Dimethylamino)ethoxy]-1-phenylbenzimidazole;
5-[3-(N,N-Dimethylamino)propoxy]-1-phenylbenzimidazole;
5-[2-(4-Morpholino)ethoxy]-1-phenylbenzimidazole;
5-[3-(4-Morpholino)propoxy]-1-phenylbenzimidazole;
Methyl 1-phenylbenzimidazole-6-carboxylate;
6-Ethoxy-1-phenylbenzimidazole;
1-(4-Aminophenyl)-5-methoxybenzimidazole;
5,6-Dihydroxy-1-phenylbenzimidazole;
5,6-Methylenedioxy-1-phenylbenzimidazole;
5-Methoxy-6-methyl-1-phenylbenzimidazole;
5-Hydroxy-6-methyl-1-phenylbenzimidazole;
Methyl 5-methoxy-1-phenylbenzimidazole-6-carboxylate;
5-Hydroxy-1-phenylbenzimidazole-6-carboxylic acid;
6-Hydroxymethyl-5-methoxy-1-phenylbenzimidazole;
5-Methoxy-1-phenylbenzimidazole-6-carboxaldehyde;
5-Methoxy-1-(2-thienyl)benzimidazole;
5-Methoxy-1-(3-thienyl)benzimidazole;
5-(4-Hydroxybutoxy)-1-phenylbenzimidazole;
5-[4-(N,N-Dimethylamino)butoxy]-1-phenylbenzimidazole;
5-[4-(4-Morpholino)butoxyl]-1]phenylbenzimidazole;
4,5-Dimethoxy-1-phenylbenzimidazole;
4,5-Dihydroxy-1-phenylbenzimidazole;
5-Hydroxy-4-methoxy-1-phenylbenzimidazole;
4-Hydroxy-5-methoxy-1-phenylbenzimidazole;
4-Bromo-5-hydroxy-1-phenylbenzimidazole;
4-Bromo-5-allyloxy-1-phenylbenzimidazole; or
5-(Methylthio)-1-phenylbenzimidazole.

DETAILED DESCRIPTION OF THE INVENTION

The present invention provides compounds of Formula I that can be used to treat or prevent cancer, restenosis, atherosclerosis, or psoriasis.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "-" means a bond.

The term "patient" means all animals including humans. Examples of patients include humans, cows, dogs, cats, goats, sheep, and pigs.

The term "substituted" means that the base organic radical has one or more substituents. For example, substituted aryl means an aryl radical that has one or more substituents. Substituents include, but are not limited to, halogen, $C_1$–$C_8$alkyl, —CN, $CF_3$, —$NO_2$, —$NH_2$, —$NHC_1$–$C_8$alkyl, —N($C_1$–$C_8$alkyl)$_2$, —$OC_1$–$C_8$alkyl, and —OH.

The term "heterocycle" means a cycloalkyl group wherein one or more carbon atom is replaced with a heteroatom. Examples of heterocycles includes, but are not limited to, pyrrolidinyl, piperidyl, and piperazinyl.

Those skilled in the art are easily able to identify patients having cancer, atherosclerosis, psoriasis, restenosis, or at risk of having atherosclerosis or restenosis. For example, patients who are at risk of having restenosis include, but are not limited to, patients having undergone balloon angioplasty or other surgical vascular procedures.

A therapeutically effective amount is an amount of a compound of Formula I, that when administered to a patient, ameliorates a symptom of the disease.

The term "cancer" includes, but is not limited to, the following cancers:
  breast;
  ovary;
  cervix;
  prostate;
  testis;
  esophagus;
  glioblastoma;
  neuroblastoma;
  stomach;
  skin, keratoacanthoma;
  lung, epidermoid carcinoma, large cell carcinoma, adenocarcinoma;
  bone;
  colon, adenocarcinoma, adenoma;
  pancreas, adenocarcinoma;
  thyroid, follicular carcinoma, undifferentiated carcinoma, papillary carcinoma;
  seminoma;
  melanoma;
  sarcoma;
  bladder carcinoma;
  liver carcinoma and biliary passages;
  kidney carcinoma;
  myeloid disorders;
  lymphoid disorders, Hodgkin's, hairy cells;
  buccal cavity and pharynx (oral), lip, tongue, mouth, pharynx;
  small intestine;
  colon-rectum, large intestine, rectum;
  brain and central nervous system; and
  leukemia.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragéees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J Pharm. Sci.*, 1977; 66: 1–19 which is incorporated herein by reference.)

Examples of pharmaceutically acceptable, non-toxic esters of the compounds of this invention include $C_1-C_6$alkyl esters wherein the alkyl group is a straight or branched chain. Acceptable esters also include $C_5-C_7$cycloalkyl esters as well as arylalkyl esters such as, but not limited to benzyl. $C_1-C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–C6alkyl amines and secondary $C_1-C_6$dialkyl amines wherein the alkyl groups are straight or branched chain. In the case of secondary amines the amine may also be in the form of a 5- or 6-membered heterocycle containing one nitrogen atom. Amides derived from ammonia, $C_1-C_3$alkyl primary amines, and $C_1-C_2$dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

EXAMPLES

The compounds of Formula I can be prepared by the processes described in the following Reaction Schemes:

Cyclization of these using formic acid and a mineral acid (preferably HCl), or using formamidine acetate in a hydroxylic solvent preferably 2-methoxyethanol) under reflux, or using trialkyl orthoformates and a general published method (H. J. Schaeffer, C. F. Schwender, *J. Med. Chem.*, 1974; 17: 6–8), gave the desired substituted 1-phenylbenzimidazoles.

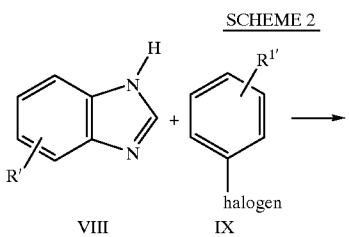

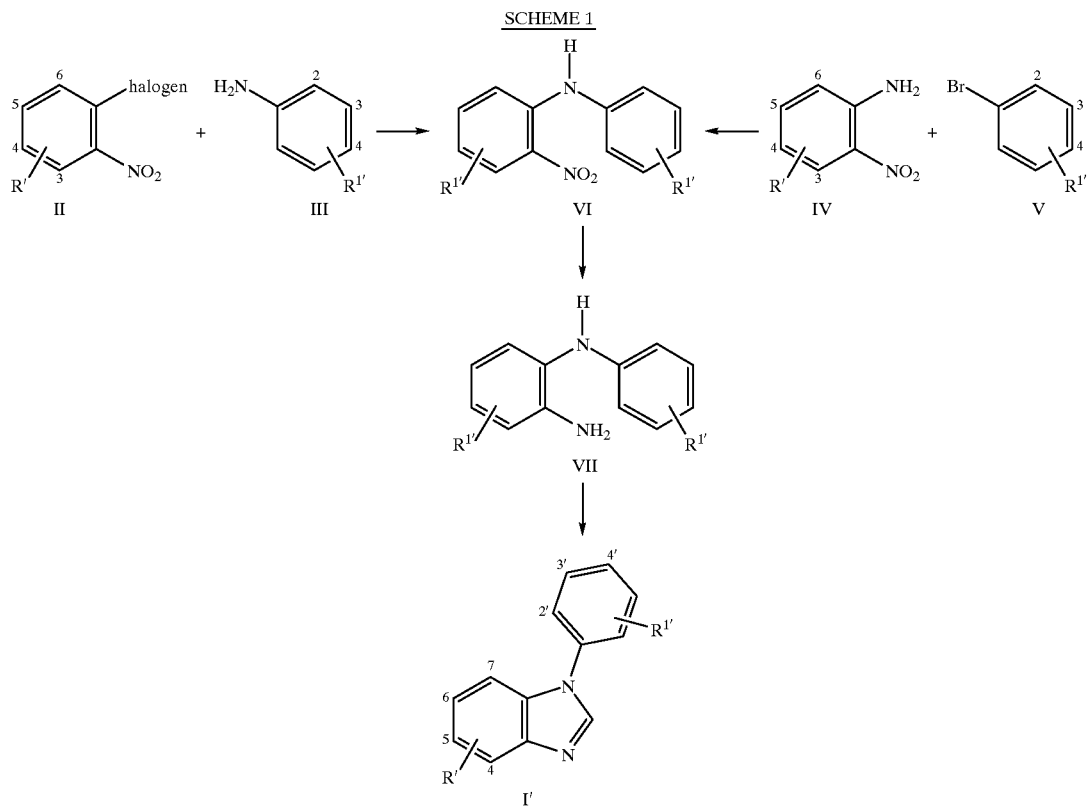

In Scheme 1, base-catalyzed condensation of substituted 2-nitrohalobenzenes (II) with substituted anilines (III), using bases such as NaOAc, NaHCO$_3$, K$_2$CO$_3$ or aliphatic amines in solvents such as EtOH or aliphatic amines, at temperatures preferably from 60–130° C., gives the substituted 2-nitrodiphenylamines (VI). Alternatively, copper-catalyzed condensation of substituted 2-nitroanilines (IV) with substituted bromobenzenes (V) under basic conditions, using Na$_2$CO$_3$, K$_2$CO$_3$ either with or without a suitable solvent, also gives the substituted 2-nitrodiphenylamines (VI). Reduction of the 2-nitrodiphenylamines (VI), preferably with Raney nickel or by hydrogenation over a palladium/carbon catalyst in a hydroxylic solvent, preferably methanol, gives the substituted 2-aminodiphenylamines (VII).

-continued

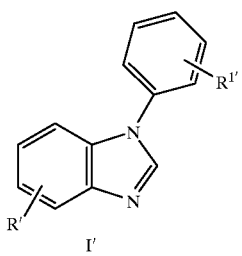

In Scheme 2, Reaction of substituted benzimidazoles (VII) with substituted halobenzenes (IX) and a base such as KH, $K_2CO_3$ or NaH in a solvent such as DMF or DMSO at 50–150° C., according to a general published procedure (M. F. Mackay, G. J. Trantino, J. F. K. Wilshire, *Aust. J. Chem.*, 1993; 46: 417–425) gave the desired substituted 1-phenylbenzimidazoles.

SCHEME 3

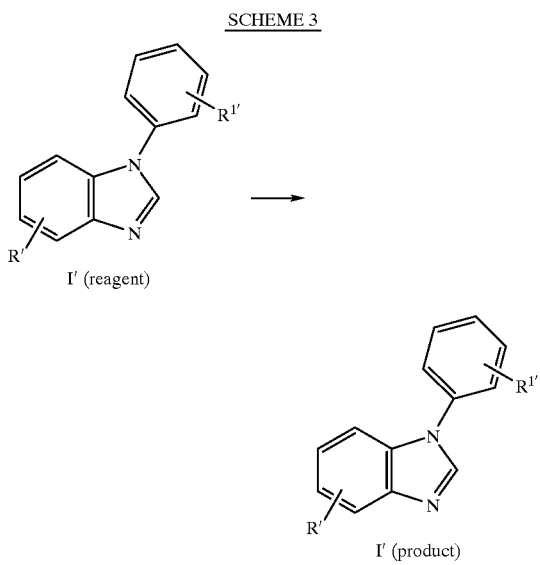

I' (reagent)

I' (product)

In Scheme 3, substituted 1-phenylbenzimidazoles of Formula I' bearing suitable substituent groups R' and $R^{1'}$ can be converted to other 1-phenylbenzimidazoles of Formula I' by appropriate transformation of the substituent groups, by known reactions. A non-exhaustive list of examples includes the conversions: OMe→OH (HBr/AcOH); $NH_2$→Cl ($NaNO_2$/CuCl); CN→COOH (90% $H_2SO_4$); $CH_2OH$→CHO ($MnO_2$); Me→COOH ($KMnO_4$); COOH→$NH_2$ ($SOCl_2/NaN_3$/heat); COOH→COOMe ($SOCl_2$/MeOH); COOH→$CONH_2$($SOCl_2/NH_3$); OH→O alkyl (base/alkyl halide); aryl H→aryl Br (N-bromosuccinimide); OH→SR([a] base/$Me_2NC(S)Cl$. [b] heat [c] aqueous KOH [d] base/alkyl halide).

SCHEME 4

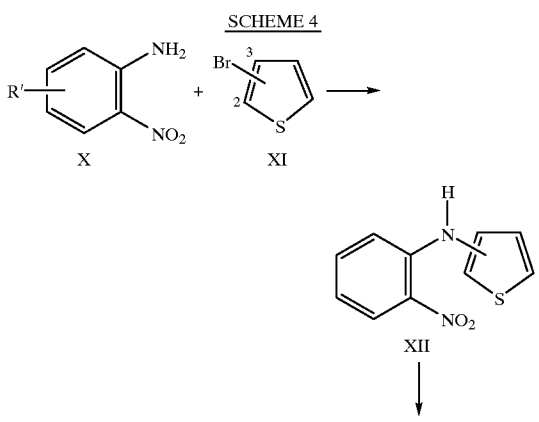

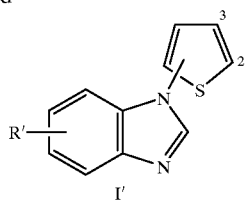

I'

In Scheme 4, condensation of substituted 2-nitroanilines (X) and haloheterocycles (e.g., bromothiophenes XI) using CuI catalyst and a base (preferably $K_2CO_3$) gave, for example, substituted 2-nitro-N-(2-thienyl)anilines (XII). Cyclization of these by one of the methods of Scheme 1 (e.g., reduction of the nitro group and reaction with formamidine acetate) gave the desired substituted 1-[(hetero) aromatic]benzimidazoles of Formula (I').

R' and $R^{1'}$ as used in Schemes 1–4 and the Examples have the same meanings as the corresponding substituents of Formula I.

The following abbreviations are used throughout this patent application:

| | |
|---|---|
| $Et_2O$ | Diethyl ether |
| EtOAc | Ethyl acetate |
| AcOH | Acetic acid |
| Me | Methyl |
| MeOH | Methanol |
| mp | melting point |
| DMF | Dimethylformamide |
| DMSO | Dimethylsulfoxide |
| THF | Tetrahydrofuran |
| MeCN | Acetonitrile |
| NaOH | Sodium hydroxide |
| DIBAL | Diisobutylaluminum hydride |
| NMR | Nuclear Magnetic Resonance |

Example 1

1-Phenylbenzimidazole was prepared by the method of H. Hofinann and J. Spindler, *Z. Chem.*, 1976; 16: 52.

Example 2

1-(3-Hydroxyphenyl)benzimidazole Hydrochloride by the Method of Scheme 3

A solution of 1-(3'-methoxyphenyl)benzimidazole hydrochloride (0.25 g, 1.11 mmol) in 48% HBr in glacial acetic acid (15 mL) was refluxed for 48 hours and concentrated to dryness. The residue was partitioned between 2N NaOH and $Et_2O$, and the aqueous portion was carefully neutralized with 2N HCl, extracted with EtOAc, and the extract worked up to give a solid which was chromatographed on silica gel. Elution with EtOAc/petroleum ether (1:1) gave Example 2 (0.22 g, 94%). HCl salt: mp (MeOH/$Et_2O$) 119° C.

$^1$H NMR ($D_2O$): δ9.44 (s, 1 H, H-2), 7.93 (dd, J=8.0, 1.0 Hz, 1 H, H-4), 7.74–7.62 (m, 3 H), 7.68–7.63 (m, 1 H), 7.56 (dd, J=8.1, 8.1 Hz, 1 H), 7.20 (dd, J=8.4, 1.6 Hz, 1 H), 7.15 (dd, J=8.3, 1.6 Hz, 1 H), 7.10 (dd, J=2.1, 2.1 Hz, 1 H, H-2').

$^{13}$C NMR: δ159.88 (s), 142.30 (d), 136.82 (s), 134.26 (d), 133.70 (s), 133.39 (s), 130.01 (d), 129.87 (d), 120.21 (d), 119.02 (d), 117.68 (d), 115.76 (d), 114.34 (d). Analysis calculated for $C_{13}H_{10}N_2O·HCl·0.25H_2O$ requires: C, 62.1; H, 4.6; N, 11.2%. Found: C, 62.3; H, 4.6; N, 11.1%.

1-(3-Methoxyphenyl)benzimidazole hydrochloride was prepared by the method of Scheme 1 as follows: A mixture of 2-fluoronitrobenzene (II: R'=H, hal=F) (7.47 mL, 0.07 mol), 3-methoxyaniline (III: R$^{1'}$=3-OMe) (7.99 mL, 0.07 mol) and K$_2$CO$_3$ (14.69 g, 0.11 mol) in DMF (60 mL) was warmed at 125° C. with stirring for 18 hours. After removal of the solvent under reduced pressure, the residue was partitioned between EtOAc and 0.5N HCl, and the EtOAc solution was worked up to give an oil. Excess 2-fluoronitrobenzene was removed by distillation under reduced pressure, and the residue was recrystallized from ethanol to give 3'-methoxy-2-nitrodiphenylamine (VI: R'=H, R$^{1'}$=3'-OMe) (1.95 g, 58%): mp (EtOH) 59–60° C.

$^1$H NMR (CDCl$_3$): δ9.45 (br, 1 H, NH), 8.19 (dd, J=8.6, 1.6 Hz, 1 H, H-3), 7.39–7.27 (m, 3 H), 6.87 (dd, J=8.1, 1.9 Hz, 1 H), 6.82–6.75 (m, 3 H), 3.82 (s, 3 H, OCH$_3$).

$^{13}$C NMR δ160.71 (s), 142.79 (s), 139.89 (s), 135.61 (d), 133.26 (s), 130.36 (d), 126.58 (d), 117.56 (d), 116.32 (2d), 111.02 (d), 109.89 (d), 55.35 (q). Analysis calculated for C$_{13}$H$_{12}$N$_2$O$_3$ requires: C, 63.9; H, 5.0; N, 11.5%. Found: C, 64.1; H, 4.8; N, 11.5%.

Reduction of 3'-methoxy-2-nitrodiphenylamine, followed by reaction with formamidine acetate, as described for the synthesis of Example 12, gave 1-(3-methoxyphenyl) benzimidazole hydrochloride, (77%): mp (MeOH/Et$_2$O) 119.5° C.

$^1$H NMR (D$_2$O): δ9.49 (s, 1 H, H-2), 7.95 (d, J=8.2 Hz, 1 H, H-4), 7.77–7.72 (m, 1 H), 7.68–7.61 (m, 3 H), 7.25 (dd, J=8.2, 2.3 Hz, 1 H, H-4'), 7.16 (dd, J=2.3, 2.1 Hz, 1 H, H-2'), 3.93 (s, 3 H, OCH$_3$).

$^{13}$C NMR: δ162.86 (s), 142.24 (d), 136.66 (s), 134.17 (d), 133.46 (s), 133.30 (s), 130.09 (d), 129.92 (d), 119.48 (d), 118.75 (d), 117.75 (d), 115.60 (d), 112.91 (d), 58.50 (q). Analysis calculated for C$_{14}$H$_{12}$N$_2$O.HCl requires: C, 64.5; H, 5.0; N, 10.7%. Found: C, 64.5; H, 5.5; N, 10.8%.

Example 3

1-(3-Aminophenyl)benzimidazole by the Method of Scheme 3

Reduction of 1-(3-nitrophenyl)benzimidazole (prepared by the method of M. A. Khan and J. B. Polya, *J. Chem. Soc.* (C), 1970: 85–91) with Raney nickel as for Example 8, followed by chromatography on silica gel, eluting with EtOAc, gave Example 3 (71%) mp (EtOAc/hexane) 93–95° C.

$^1$H NMR [(CD$_3$)$_2$SO]; δ5.52 (s, 2 H), 6.66 (dd, J=2.2, 8.2 Hz, 1 H), 6.73 (d, J=7.0 Hz, 1 H), 6.80–6.82 (m, 1 H), 7.23 (t, J=8.0 Hz, 1 H), 7.27–7.35 (m, 2H) 7.61 (d, J=7.1 Hz, 1 H), 7.76 (d, J=7.4 Hz, 1 H), 8.47 (s, 1 H); MS(CI) (m+1)/z 210. Analysis calculated for C$_{13}$H$_{11}$N$_3$ requires: C, 74.6; H, 5.3; N, 20.1%. Found: C, 74.8; H, 5.5; N, 19.9%.

Example 4

1-(3-Formylphenyl)benzimidazole Hydrochloride by the Method of Scheme 2

A solution of benzimidazole (VIII: R=H) (1.00 g, 8.47 mmol) and 3-fluorobenzaldehyde (IX: R$^{1'}$=3-CHO; halogen=F) (1.08 mL, 10.2 mmol) in DMSO (30 mL) was heated with anhydrous K$_2$CO$_3$ (2.34 g, 16.9 mmol) for 24 hours at 100° C. to give, after column chromatography on silica gel eluting with EtOAc/hexane (1:1) to EtOAc/hexane (3:1), Example 4 as the HCl salt, mp (EtOAc/MeOH) 196–201° C.

$^1$H NMR [(CD$_3$)$_2$SO]: δ10.16 (s, 1 H, CHO), 9.40 (s, 1 H, H-2), 8.30 (t, J=1.6 Hz, 1 H, H-2'), 8.13 (m, 2 H, aromatic), 7.93 (m, 2 H, aromatic), 7.78 (m, 1 H, aromatic), 7.55 (m, 2 H, H-5, 6). Analytical calculated for C$_{14}$H$_{10}$N$_2$O.HCl.0.5H$_2$O requires: C, 62.8; H, 4.5; N, 10.5%. Found: C, 63.0; H, 4.4; N, 10.5%.

Example 5

1-(4-Methoxyphenyl)benzimidazole Hydrochloride by the Method of Scheme 1

Reduction of 4'-methoxy-2-nitrodiphenylamine (VI, R'=H, R$^{1'}$=4-OCH$_3$) followed by reaction with formamidine acetate as described for synthesis of Example 12 gave Example 5 as the hydrochloride salt, (76%), mp 214–215° C. (MeOH/Et$_2$O) (F. Montanari and R. Passerini, *Boll. sci. facolta chim. ind. Bologna,* 1953; 11: 42–45; CA 48: 6436b record a mp of 99° C. for the free base form of Example 5).

$^1$H NMR (D$_2$O): δ9.47 (s, 1 H, H-2), 7.96 (d, J=8.3 Hz, 1 H, H-4), 7.76 (ddd, J=8.3, 8.2, 0.7 Hz, 1 H, H-6), 7.66 (ddd, J=8.4, 8.2, 0.7 Hz, 1 H, H-5), 7.59 (d, J=8.4 Hz, 1 H, H-7), 7.57 (d, J=9.0 Hz, 2 H, H-2', 6'), 7.19 (d, J=9.0 Hz, 2 H, H-3',5'), 3.98 (s, 3 H, OCH$_3$).

$^{13}$C NMR: δ162.78 (s), 141.97 (d), 133.45 (s), 133.03 (s), 129.98 (d), 129.79 (d), 128.47 (s), 128.42 (d), 118.03 (d), 117.62 (d), 115.35 (d), 58.44 (q). Analytical calculated for C$_{14}$H$_{12}$N$_2$O.HCl requires: C, 64.5; H, 5.0; N, 10.7%. Found: C, 64.6; H, 5.2; N, 10.8%.

4'-Methoxy-2-nitrodiphenylamine (VI, R'=H, R$^{1'}$=4-OCH$_3$) was prepared by reaction of 2-fluoronitrobenzene and p-anisidine as described above for synthesis of the isomeric 3'-methoxy-2-nitrodiphenylamine (61%), mp 88–89° C. (MeOH).

$^1$H NMR (CDCl$_3$): δ9.40 (br, 1 H, NH), 8.18 (dd, J=8.6, 1.5 Hz, 1 H, H-3), 7.32 (ddd, J=8.7, 8.6, 0.9 Hz, 1 H, H-5), 7.19 (d, J=8.8 Hz, 2 H, H-2', 6'), 7.00 (dd, J=8.7, 0.9 Hz, 1 H, H-6), 6.95 (d, J=8.8 Hz, 2 H, H-3', 5'), 6.71 (ddd, J=8.6, 8.6, 0.9 Hz, 1 H, H-4), 3.84 (s, 3 H, OCH$_3$).

$^{13}$C NMR: δ157.88 (s), 144.44 (s), 135.67 (d), 132.41 (s), 131.13 (s), 127.05 (d), 126.53 (d), 116.71 (d), 115.70 (d), 114.92 (d), 55.48 (q). Analytical calculated for C$_{13}$H$_{12}$N$_2$O$_3$ requires: C, 63.9; H, 4.9; N, 11.5%. Found: C, 63.5; H, 5.0; N, 11.3%.

Example 6

1-(4-Hydroxyphenyl)benzimidazole Hydrochloride by the Method of Scheme 3

Reaction of 1-(4'-methoxyphenyl)benzimidazole hydrochloride with HBr in glacial acetic acid, as described above for synthesis of Example 2, gave Example 6 as the hydrochloride salt, (86%), mp 255° C. (MeOH/Et$_2$O) (M. Tashiro, T. Itoh and G. Fukata, *Synthesis,* 1982: 217–219 report a mp of 192–195° C. for the free base form of Example 6).

$^1$H NMR (D$_2$O): δ9.52 (s, 1 H, H-2), 7.99 (d, J=8.4 Hz, 1 H, H-4), 7.79–7.71 (m, 3 H, H-5, 6,7), 7.63 (d, J=8.8 Hz, 2 H, H-2',6'), 7.17 (d,J=8.8 Hz, 2 H, H-3'5').

$^{13}$C NMR: δ159.92 (s), 141.98 (d), 133.35 (s), 132.60 (s), 129.30 (d), 129.26 (d), 128.60 (d), 127.08 (s), 118.87 (d), 117.09 (d), 114.97 (d). Analytical calculated for C$_{13}$H$_{10}$N$_2$O.HCl requires: C, 63.2; H, 4.5; N, 11.4%. Found: C, 62.8; H, 4.5; N, 11.4%.

Example 7

1-(4-Carbomethoxyphenyl)benzimidazole by the Method of Scheme 2

Reaction of benzimidazole (VIII: R'=H) and methyl 4-fluorobenzoate (IX: R$^{1'}$=COOMe; halogen=F) using a published procedure [M. F. Mackay, G. J. Trantino, J. F. K. Wilshire, *Aust. J. Chem.*, 1993; 46: 417–425], using DMF as solvent, followed by chromatography on silica gel, eluting with EtOAc/hexane/CH$_2$Cl$_2$ (5:3:2), gave Example 7 (50%), mp 105–107° C.

$^1$H NMR [(CD$_3$)$_2$SO]: δ3.91 (s, 3 H), 7.30–7.40 (m, 2 H), 7.73 (d, J=6.8 Hz, 1H), 7.80 (d, J=7.0 Hz, 1 H), 7.89 (d, J=8.7 Hz, 2 H), 8.19 (d, J=8.7 Hz, 2 H), 8.69 (s, 1 H); MS(CI) (m+1)/z 253. Analysis calculated for C$_{15}$H$_{12}$N$_2$O$_2$ requires: C, 71.4; H, 4.8; N, 11.1%. Found: C, 71.8; H, 4.9; N, 11.1%.

Example 8

1-(4-Aminophenyl)benzimidazole Dihydrochloride by the Method of Scheme 3

Raney nickel (0.5 g) was added to a solution of 1-(4-nitrophenyl)-benzimidazole (prepared by the method of M. A. Khan and J. B. Polya, *J. Chem. Soc. (C)*, 1970: 85–91) (1.5 g, 6.3 mmol) in THF (100 mL) under nitrogen. The nitrogen was exchanged for hydrogen and stirred overnight, then filtered. The filtrate was concentrated, and the residue was chromatographed on silica gel, eluting with EtOAc/hexane (3:1) followed by EtOAc to give Example 8 as an oil. This was dissolved in Et$_2$O/MeCN (1:1, 200 mL) and treated with HCl gas to give the dihydrochloride salt (1.4 g, 79%), mp 278–281° C. (F. Montanari and R. Passerini, *Boll. sci. facolta chim. ind. Bologna*, 1953, 11, 42–45; CA 48: 6436b record a mp of 116° C. for the free base form of Example 8).

$^1$H NMR [(CD$_3$)$_2$SO]: δ7.34 (d, J=8.4 Hz, 2 H), 7.58–7.67 (m, 2H), 7.7–7.8 (m 3 H), 7.96 (d, J=7.0 Hz, 1 H), 9.82 (s, 1 H); MS(CI) (m+1)/z 210. Analysis calculated for C$_{13}$H$_{11}$N$_3$.2HCl.0.25H$_2$O requires: C, 54.7; H, 4.8; N, 14.7%. Found: C, 54.5; H, 4.8; N, 14.6%.

Example 9

1-(4-Formylphenyl)benzimidazole by the Method of Scheme 2

Reaction of benzimidazole (VIII: R'=H) with 4-fluorobenzaldehyde (IX: R$^1$'=4-CHO; halogen=F) using a published procedure [M. F. Mackay, G. J. Trantino, J. F. K. Wilshire, *Aust. J. Chem.*, 1993; 46: 417–425], using DMF as the solvent, followed by chromatography on silica gel, eluting with EtOAc/hexane/CH$_2$Cl$_2$ (1:4:1 followed by 10:10:1), gave Example 9 (58%), mp (EtOAc/hexane) 98–99° C. (I. Sircar, B. L. Duell, J. A. Bristol, R. E. Weishaar, and D. B Evans, J. Med. Chem., 1987; 30: 1023–1029 report a mp of 100–101° C. for Example 9).

$^1$H NMR [(CD$_3$)$_2$SO]: δ7.30–7.40 (m, 2 H), 7.77 (d, J=7.0 Hz, 1 H), 7.82 (d, J=7.0 Hz, 1 H), 7.98 (d, J=8.4 Hz, 2 H), 8.16 (d, J=8.7 Hz, 2 H), 8.72 (s, 1 H), 10.11 (s, 1 H); MS(CI) (m+1)/z 223. Analysis calculated for C$_{14}$H$_{10}$N$_2$O requires: C, 75.7; H, 4.5; N, 12.6%. Found: C, 75.7; H, 4.6; N, 12.6%.

Example 10

1-(4-Pyridinyl)benzimidazole dihydrochloride was prepared by the method of M. A. Khan and J. B. Polya, *J Chem. Soc. (C)*, 1970: 85–91.

Example 11

4-Hydroxy-1-phenylbenzimidazole Hydrochloride by the Method of Scheme 3

Demethylation of 4-methoxy-1-phenylbenzimidazole hydrochloride with HBr in glacial acetic acid as described for synthesis of Example 2 gave Example 11 as the HCl salt, (77%): mp (MeOH/Et$_2$O) 238–240° C.

$^1$H NMR (D$_2$O): δ9.41 (s, 1 H, H-2), 7.74–7.67 (m, 5 H, Ph), 7.47 (dd,J=8.3, 8.2 Hz, 1 H, H-6), 7.22 (d, J=8.3 Hz, 1 H, H-7), 7.08 (dd, J=8.2 Hz, 1 H, H-5);

$^{13}$C NMR: δ147.45 (s), 141.70 (d), 136.00 (s), 135.85 (s), 133.32 (d), 133.10 (d), 131.01 (d), 127.47 (d), 123.81 (s), 114.17 (d), 106.90 (d). Analytical required for C$_{13}$H$_{10}$N$_2$O.HCl.0.25H$_2$O: C, 62.2; H, 4.6; N, 11.4%. Found: C, 62.5; H, 4.4; N, 11.2%.

4-Methoxy-1-phenylbenzimidazole hydrochloride was prepared by the method of Scheme 1 as follows: A suspension of 3-methoxy-2-nitroaniline (IV: R'=3-OMe) (5.00 g, 0.030 mol), K$_2$CO$_3$ (2.21 g, 0.016 mol) and cuprous iodide (50 mg, 0.26 mmol) in bromobenzene (V: R$^1$'=H) (10 mL) was refluxed with vigorous stirring for 18 hours, and the excess of bromobenzene was removed under reduced pressure. The residue was partitioned between EtOAc and water, filtered through Celite, and the organic layer worked up and chromatographed on silica gel. EtOAc/petroleum ether (1:19) eluted 3-methoxy-2-nitrodiphenylamine (VI: R'=3-OMe, R$^1$'=H) (4.00 g, 54%): mp (aqueous MeOH) 95° C.

$^1$H NMR (CDCl$_3$): δ7.52 (br, 1 H, NH), 7.33 (dd, J=8.6, 8.3 Hz, 1 H, H-5), 7.23–7.08 (m, 5 H, Ph), 6.84 (dd, J=8.6, 0.8 Hz, 1 H, H-6), 6.44 (dd, J=8.3, 0.8 Hz, 1 H, H-4), 3.91 (s, 3 H, OCH$_3$).

$^{13}$C NMR: δ154.33 (s), 140.32 (s), 140.06 (s), 132.70 (d), 129.51 (d), 123.96 (d), 121.82 (d), 108.86 (d), 102.57 (d), 56.53 (q). Analysis calculated for C$_{13}$H$_{12}$N$_2$O$_3$ requires: C, 63.8; H, 5.0; N, 11.5%. Found: C, 63.8; H, 4.9; N, 11.4%.

Reduction of the above nitrodiphenylamine with H$_2$/Pd—C followed by reaction of the crude phenylenediamine with formamidine acetate, as for the synthesis of Example 12, gave 4-methoxy-1-phenylbenzimidazole as the HCl salt (74%): mp 191–193° C.

$^1$H NMR (D$_2$O): δ9.35 (s, 1 H, H-2), 7.71–7.70 (m, 3 H, Ph), 7.64–7.62 (m, 2 H, Ph), 7.53 (dd, J=8.4, 8.1 Hz, 1 H, H-6), 7.24 (d, J=8.4 Hz, 1 H, H-7), 7.15 (d, J=8.1 Hz, 1 H, H-5), 4.08 (s, 3 H, OCH$_3$). $^{13}$C NMR: δ150.50 (s), 141.65 (d), 135.98 (s), 135.31 (s), 133.24 (d), 133.11 (d), 130.96 (d), 127.28 (d), 124.57 (s), 110.09 (d), 107.48 (d), 59.02 (q). Analysis calculated for C$_{14}$H$_{12}$N$_2$O.HCl requires: C, 64,5; H, 5.0; N, 10.7%. Found: C, 64.4; H, 5.0; N, 10.6%.

Example 12

5-Methyl-1-phenylbenzimidazole Hydrochloride by the Method of Scheme 1

A mixture of 4-chloro-3-nitrotoluene (II: R'=4-Me, halogen=Cl) (1.00 mL, 7.56 mmol), aniline (III: R$^1$'=H) (6.89 mL, 0.075 mmol) and sodium acetate (1.24 g, 0.015 mol) was refluxed under nitrogen for 18 hours. The cooled product was partitioned between EtOAc and water, and the organic portion was washed with 2N HCl, then brine, and worked up to give an oil which was chromatographed on silica gel. Elution with petroleum ether gave the 4-methyldiphenylamine (VI: R'=4-Me, R$^1$'=H) as an orange oil (1.01 g, 58%) which was used directly. A solution of this (1.01 g, 4.42 mmol) in 1:1 MeOH/EtOAc (60 mL) was hydrogenated over 5% Pd—C for 3 hours. After removal of the catalyst and concentration to dryness under reduced pressure, the residue was dissolved in 2-methoxyethanol (100 mL) containing formamidine acetate (0.92 g, 8.84 mmol) and the solution refluxed for 3 hours. After removal of the solvent under reduced pressure, the residue was partitioned between EtOAc and water. The organic portion was worked up to give an oil which was chromatographed on silica gel. Elution with EtOAc/petroleum ether (1:5) gave foreruns, while EtOAc/petroleum ether (1:1) gave Example 12 (0.91 g, 98%). HCl salt: mp (MeOH/Et$_2$O) 196–200° C.

$^1$H NMR (D$_2$O): δ9.40 (s, 1 H, H-2), 7.76–7.72 (m, 3 H, Ph), 7.68 (br s, 1 H, H-4),7.63–7.59 (m,2H, Ph),7.50 (d, J=8.6 Hz, 1 H, H-7),7.43 (br d, J=8.6 Hz, 1 H, H-6),2.55 (s, 3 H, CH$_3$).

$^{13}$C NMR: δ114.66 (d), 141.08 (s), 135.74 (s), 133.54 (s), 133.28 (d), 133.15 (d), 131.68 (s), 131.37 (d), 127.04 (d), 116.93 (d), 115.07 (d), 23.38 (q). Analysis calculated for C$_{14}$H$_{12}$N$_2$.HCl requires: C, 68.7; H5.4; N, 11.5%. Found: C, 68.9; H, 5.6; N, 11.6%.

Example 13

5-Methoxy-1-phenylbenzimidazole Hydrochloride by the Method of Scheme 1

A mixture of 4-methoxy-2-nitroaniline (IV, R'=OCH$_3$) (10.0 g, 59 mmol) K$_2$CO$_3$ (16.4 g, 120 mmol), CuI (0.20 g, 1.05 mmol) and bromobenzene (V, R$^{1'}$=H) (30 mL) was heated under reflux in nitrogen for 48 hours. Excess bromobenzene was removed under reduced pressure, the residue was partitioned between EtOAc and water, and the mixture was filtered through Celite. The organic layer was then worked up, and the residue was chromatographed on silica gel. Petroleum ether eluted 4-methoxy-2-nitrodiphenylamine (VI, R'=4-OCH$_3$, R$^{1'}$=H) (8.92 g, 62%), which was used directly. Hydrogenation of this over Pd—C in MeOH, and treatment of the product with formamidine acetate as described above for synthesis of Example 12, gave Example 13 as the hydrochloride salt (7.54 g, 49% overall): mp (MeOH/Et$_2$O) 190–193° C. (Y. S. Tsizin and S. A. Chemyak, *Khim. Geterotsikl. Soedin.*, 1978;12: 1680–1683; CA 90: 137728 have reported the synthesis of Example 13).

$^1$H NMR (D$_2$O): δ9.39 (s, 2 H, H-2), 7.76–7.72 (m, 3 H, Ph), 7.65–7.61 (m, 2 H, Ph), 7.55 (d, J=9.2 Hz, 1 H, H-7), 7.37 (d, J=2.3 Hz, 1 H, H-4), 7.19 (dd, J=9.2, 2.3 Hz, 1 H, H-6), 3.95 (s, 3 H, OCH$_3$);

$^{13}$C NMR: δ161.43 (s), 141.60 (d), 136.76 (s), 134.58 (s), 133.32 (d), 133.16 (d), 128.28 (s), 127.05 (d), 119.74 (d), 116.57 (d), 99.78 (d), 58.84 (q). Analysis calculated for C$_{14}$H$_{12}$N$_2$O.HCl requires: C, 64.5; H, 5.0; N, 10.7%. Found: C, 64.3; H, 5.1; N, 10.6%.

Example 14

5-Hydroxy-1-phenylbenzimidazole by the Method of Scheme 3

Demethylation of 5-methoxy- 1-phenylbenzimidazole hydrochloride with HBr in glacial acetic acid, as described above for preparation of Example 2 gave Example 14 (83%): mp (EtOAc/hexane) 247–249° C. (K. Fries, *Ann.*, 1927;454: 207 reports a mp of 244° C. for Example 14).

$^1$H NMR [(CD$_3$)$_2$SO]: δ9.25 (s, 1 H), 8.43 (s, 1 H), 7.60–7.70 (m, 4 H), 7.40–7.50 (m, 2 H), 7.07 (d, J=2.4 Hz, 1 H), 6.82 (dd, J=8.7, 2.4 Hz, 1 H). Analysis calculated for C$_{13}$H$_{10}$N$_2$O requires: C, 74.3; H, 4.8; N, 13.3%. Found: C, 74.3; H, 5.0; N, 13.2%.

Example 15

5-Chloro-1-phenylbenzimidazole by the Method of Scheme 1

Reaction of 5-chloro-2-nitrodiphenylamine (VI, R'=4-Cl, R$^{1'}$=H) with Raney nickel in MeOH gave 5-chloro-2-aminodiphenylamine (VII, R=4-Cl, R$^{1'}$=H) (97%), which was used directly. Reaction of this with formic acid, followed by chromatography of the product on silica gel, eluting with EtOAc/hexane (1:1), gave Example 15 (71%), mp 95–97° C. (F. Montanari and R. Passerini, *Boll. sci. facolta chim. ind. Bologna,* 1953; 11: 42–45; CA 48: 6436b, record a mp of 118° C. for Example 15).

$^1$H NMR [(CD$_3$)$_2$SO]: δ7.35 (dd, J=2.1, 8.6 Hz, 1 H), 7.4–7.5 (m, 1 H), 7.5–7.7 (m, 5 H), 7.74 (d, J=8.8 Hz, 1 H), 8.57 (s, 1 H); MS(CI) (m+1)/z 229. Analysis calculated for C$_{13}$H$_9$ClN$_2$ requires: C, 68.3; H, 4.0; N, 12.2%. Found: C, 68.4; H, 4.1; N, 12.3%.

Example 16

1-Phenylbenzimidazole-5-carboxylic Acid Hydrochloride by the Method of Scheme 3

A solution of the ester Example 17 (1.00 g, 4.20 mmol) and 2N NaOH (10 mL) in MeOH (60 mL) was stirred at 20° C. for 1 hour, then concentrated under reduced pressure to small volume. The residue was diluted with water, washed with Et$_2$O, and carefully neutralized with 3N HCl to precipitate Example 16 (0.92 g, 97%). HCl salt; mp (MeOH/Et$_2$O) 240° C. (dec.).

$^1$H NMR [D$_2$O/(CD$_3$)$_2$ SO]: δ9.66 (s, 1 H, H-2), 8.55 (d, J=0.8 Hz, 1 H, H-4), 8.23 (dd, J=8.7, 0.8 Hz, 1 H, H-6), 7.89 (d, J=8.7 Hz, 1 H, H-7), 7.77 (br s, 5 H, Ph).

$^{13}$C NMR: δ170.37 (s), 144.74 (d), 136.39 (s), 135.09 (s), 133.48 (s), 133.06 (d), 132.82 (d), 130.96 (s), 130.10 (d), 126.95 (d), 119.72 (d), 115.57 (d). Analysis calculated for C$_{14}$H$_{10}$N$_2$O$_2$.HCl.1.5H$_2$O requires: C, 55.7; H, 4.7; N, 9.3%. Found: C, 55.7; H, 4.1; N, 9.3%.

Example 17

Methyl 1-Phenylbenzimidazole-5-carboxylate by the Method of Scheme 1

A mixture of 4-chloro-3-nitrobenzoic acid (II: R'=4-COOH, halogen=Cl) (5.70 g, 0.023 mol), aniline (III: R$^{1'}$=H) (3.17 mL, 0.035 mol), N-methylmorpholine (3.24 mnL, 0.025 mol) and copper powder (0.10 g) in isoamyl alcohol (200 mL) was refluxed for 18 hours. The cooled solution was filtered through Celite and the filtrate concentrated to dryness under reduced pressure. The residue was dissolved in EtOAc, washed well the 3N HCl, then water, and finally extracted with saturated aqueous Na$_2$CO$_3$. Acidification of the extract afforded the 4-carboxydiphenylamine (VI: R=4-COOH, R$^{1'}$=H) as an orange solid (1.64 g, 28%) which was dissolved in MeOH (50 mL). The solution was saturated with gaseous HCl and then refluxed for 18 hours. After concentration to dryness the residue was partitioned between EtOAc and water, and the organic portion was worked up to give crude ester (VI: R'=4-COOMe, R$^{1'}$=H) as a yellow solid (100%). This material was dissolved in MeOH/EtOAc (1:1) (50 mL) and hydrogenated over 5% Pd—C, then treated with formamidine acetate as described above for the synthesis of Example 12. Workup gave an oil which was chromatographed on silica gel. EtOAc/petroleum ether (1:1) gave Example 17 (1.27 g, 23% overall), mp 100–102° C.

$^1$H NMR [(CD$_3$)$_2$SO]: δ3.90 (s, 3 H), 7.5–7.6 (m, 1 H), 7.6–7.8 (m, 5 H), 7.96 (dd, J=1.5, 8.5 Hz, 1 H), 8.36 (d, J=1.2, 1 H), 8.74 (s, 1 H); MS(CI) (m+1)/z 253. Analysis calculated for C$_{15}$H$_{12}$N$_2$O$_2$ requires: C, 71.4; H, 4.8; N, 11.1%. Found: C, 71.5; H, 4.9; N, 11.0%.

Example 18

1-Phenylbenzimidazole-5-carboxamide Hydrochloride by the Method of Scheme 3

Reaction of the acid chloride [obtained from the acid Example 16 as described above] with aqueous ammonia gave Example 18 (74%): mp (MeOH/Et$_2$O) 225° C. (dec.).

¹H NMR [D₂O/(CD₃)₂SO]: δ9.59 (s, 1 H, H-2), 8.37 (br s, 1 H, H-4), 8.04 (dd, J=8.8, 1.4 Hz, 1 H, H-6), 7.87 (d, J=8.8 Hz, 1 H, H-7), 7.80–7.72 (m, 5 H, Ph).

¹³C NMR: δ173.27 (s), 144.99 (d), 136.18 (s), 135.66 (s), 134.36 (s), 133.39 (d), 133.22 (d), 128.59 (d), 127.31 (d), 118.08 (d), 116.06 (d). Analysis calculated for C₁₄H₁₁N₃O.HCl.0.25H₂O requires: C, 60.4; H, 4.5; N, 15.1%. Found: C, 60.2; H, 4.5; N, 15.3%.

Example 19

5-Amino-1-phenylbenzimidazole was prepared by the method of M. A. Phillips, *J Chem. Soc.*, 1929: 2820–2828.

Example 20

5-Acetyl-1-phenylbenzimidazole by the Method of Scheme 1

Raney nickel (1.0 g) was added to a solution of 4-anilino-3-nitroacetophenone (VI: R'=4-COMe; R¹'=H) (2.0 g, 7.8 mmol) in THF (100 mL) under nitrogen. The nitrogen was exchanged for hydrogen, and the mixture was stirred for 15.5 hours, then filtered and concentrated to give crude 4-anilino-3-aminoacetophenone (VII: R=4-COMe; R¹'=H) (1.5 g, 87%). Reaction of this with formic acid using a known procedure [L. J. Mathias, C. G. Overberger, *J. Org. Chem.*, 1978;43: 3518], followed by chromatography of the product on silica gel, eluting with EtOAc/hexane (1:1), gave Example 20 (68%): mp 106–108° C.

¹H NMR [(CD₃)₂SO]: δ2.68 (s, 3 H), 7.55 (t, J=7.2 Hz, 1 H), 7.6–7.8 (m, 5 H) 7.95 (dd, J=1.5, 8.5 Hz, 1 H), 8.46 (d, J=1.2, 1 H), 8.74 (s, 1 H); MS(CI) (m+1)/z 237. Analysis calculated for C₁₅H₁₂N₂O requires: C, 76.3; H, 5.1; N, 11.9%. Found: C, 76.3; H, 5.0; N, 11.8%.

Example 21

1-Phenylbenzimidazole-5-carboxaldehyde by the Method of Scheme 3

A solution of 5-(hydroxymethyl)-1-phenylbenzimidazole (0.15 g, 0.67 mmol) made as described in Example 26 and MnO₂ (0.36 g) in CHCl₃ (10 mL) was stirred overnight, then filtered through Celite and concentrated. The residue was recrystallized from EtOAc/hexane to give Example 21 (0.10 g, 70%); mp 114–116° C.

¹H NMR [(CD₃)₂SO]: δ7.56 (t, J=7.2 Hz, 1 H), 7.6–7.7 (m, 2 H), 7.7–7.8 (m, 4 H), 8.38 (s, 1 H), 8.78 (s, 1 H), 10.11 (s, 1 H); MS(CI) (m+1)/z 223. Analysis calculated for C₁₄H₁₀N₂O requires: C, 75.7; H, 4.5; N, 12.6%. Found: C, 75.3; H, 4.7; N, 12.5%.

Example 22

1-Phenylimidazo-1H-imidazol[4,5-c]pyridine Hydrochloride by the Method of Scheme 1

A solution of 4-chloro-3-nitropyridine (II: R'=4-aza, halogen=Cl) (3.22 g, 0.020 mol), aniline (III: R¹'=H) (1.85 mL, 0.020 mol) and conc. HCl (0.17 mL, 0.02 mol) in 1:1 water/2-methoxyethanol (40 mL) was refluxed for 18 hours, then concentrated to dryness. The residue was partitioned between saturated aqueous NaHCO₃ and EtOAc, and the organic portion was worked up to give an oil which was chromatographed on silica gel. Petroleum ether eluted foreruns, while EtOAc/petroleum ether (1:1) gave 4-(N-phenylamino)-3-nitropyridine (VI: R'=4-aza, R¹'=H) (2.02 g, 41%); mp (EtOAc/petroleum ether) 119° C.

¹H NMR (CDCl₃): δ9.67 (br s, 1 H, NH), 9.28 (s, 1 H, H-2), 8.25 (dd, J=6.1, 0.8 Hz, 1 H, H-6), 7.51–7.46 (m, 2 H, Ph), 7.38–7.34 (m, 1 H, Ph), 7.31–7.28 (m, 2 H, Ph), 6.94 (d, J=6.1 Hz, 1 H, H-5).

¹³C NMR: δ153.18 (d), 149.08 (d), 147.53 (s), 136.48 (s), 130.03 (s), 130.03 (s), 130.03 (d), 125.36 (d), 109.13 (d). Analysis calculated for C₁₁H₉N₃O₂ requires: C, 61.4; H, 4.2; N, 19.5%. Found: C, 61.2; H, 4.1; N, 19.6%.

Reduction of the above nitropyridine, followed by reaction with formamidine acetate as described for synthesis of Example 12, gave Example 22 (84%). HCl salt: mp (MeOH/Et₂O) 231–232° C.

¹H NMR (D₂O): δ9.43 (s, 1 H, H-2), 9.00 (s, 1 H, H-4), 8.68 (d, J=6.7 Hz, 1 H, H-7), 8.20 (d, J=6.7 Hz, 1 H, H-6), 7.76–7.66 (m, 5 H, Ph).

¹³C NMR: δ153.34 (d), 146.29 (s), 142.53 (s), 137.82 (d), 137.04 (d), 136.14 (s), 133.15 (d), 132.76 (d), 127.05 (d), 112.48 (d). Analysis calculated for C₁₂H₉N₃.HCl requires: C, 62.2; H, 4.4; N, 18.4%. Found: C, 62.2; H. 4.5; N, 18.1%.

Example 23

5-Acetamido-1-phenylbenzimidazole Hydrochloride by the Method of Scheme 3

To a solution of the dihydrochloride salt of the amine Example 19 (0.10 g, 0.39 mmol) in water (20 mL) was added acetic anhydride (0.15 mL, 1.59 mmol) followed immediately by saturated aqueous sodium acetate solution (5 mL). After vigorous stirring for 15 minutes, the mixture was extracted with EtOAc and the extract worked up to give the amide Example 23. HCl salt (84 mg, 84%): mp (MeOH/Et₂O) 211–215° C. (hygroscopic powder).

¹H NMR (D₂O): δ9.46 (s, 1 H, H-2), 8.09 (d, J=1.9 Hz, 1 H, H-4), 7.77–7.73 (m, 3 H, Ph), 7.66–7.63 (m, 2 H, Ph), 7.61 (d, J=9.1 Hz, 1 H, H-7), 7.44 (dd, J=9.1, 1.9 Hz, 1 H, H-6), 2.15 (s, 3 H, CH₃).

¹³C NMR: δ175.51 (s), 142.61 (d), 139.34 (s), 135.59 (s), 133.65 (s), 133.41 (d), 133.22 (d), 130.37 (s), 126.98 (d), 123.45 (d), 116.27 (d), 108.73 (d), 25.81 (q). Analysis calculated for C₁₅H₁₃N₃O.HCl.H₂O requires: C, 58.9; H, 5.3; N, 13.7%. Found: C, 58.6; H, 5.3; N, 13.5%.

Example 24

5-Propionamido-1-phenylbenzimidazole Hydrochloride by the Method of Scheme 3

Reaction of Example 19 with propionic anhydride as described for Example 23 gave Example 24 (91%): mp (MeOH/Et₂O) 218–222° C.

¹H NMR (D₂O): δ9.39 (s, 1 H, H-2), 8.13 (d, J=1.8 Hz, 1 H, H-4), 7.75–7.66 (m, 6 H, Ph and H-7), 7.49 (dd, J=9.1, 1.8 Hz, 1 H, H-6), 2.47 (q, J =7.6 Hz, 2 H, CH₂CH₃), 1.22 (t, J=7.6 Hz, 3 H, CH₂CH₃).

¹³C NMR: δ179.67 (s), 142.99 (d), 139.09 (s), 135.89 (s), 134.33 (s), 133.32 (d), 133.17 (d), 131.07 (s), 127.30 (d), 123.87 (d), 116.31 (d), 109.69 (d), 32.62 (t), 11.95 (q). Analysis calculated for C₁₆H₁₅N₃O.HCl.0.25H₂O requires: C, 62.7; H, 5.4; N, 13.7%. Found: C, 62.6; H, 5.4; N, 13.4%.

Example 25

5-Acrylamido-1-phenylbenzimidazole by the Method of Scheme 3

Acryloyl chloride (0.12 mL, 1.47 mmol) was added dropwise with stirring to a stirred solution of the free base of the amine Example 19 (0.28 g, 1.34 mmol) and Et$_3$N (0.22 mL, 1.60 mmol) in CH$_2$Cl$_2$ (20 mL). After 30 minutes, the solution was washed with saturated NaHCO$_3$ solution, then water, and worked up to give an oil which was chromatographed on silica gel. EtOAc eluted foreruns, followed by Example 25 as a glass (0.10 g, 28%): mp (CH$_2$Cl$_2$/petroleum ether at −20° C.) 180–182° C.

$^1$H NMR [(CD$_3$)$_2$SO]: δ10.25 (br s, 1 H, NH), 8.56 (s, 1 H, H-2), 8.27 (d, J=1.6 Hz, 1 H, H-4), 7.71–7.64 (m, 4 H, Ph), 7.61 (d, J=8.8 Hz, 1 H, H-7), 7.54 (dd, J=8.8, 1.6 Hz, 1 H, H-6), 7.51–7.48 (m, 1 H, Ph), 6.49 (dd, J=16.9, 10.1 Hz, 1 H, CH=CH$_2$), 6.29 (dd, J=16.9, 1.9 Hz, 1 H, CH=CHH), 5.77 (dd, J=10.1, 1.9 Hz, 1 H, CH=CHH).

$^{13}$C NMR: δ162.94 (s), 143.90 (s), 143.70 (d), 135.89 (s), 134.29 (s), 131.95 (d), 130.00 (d), 129.41 (s), 127.55 (d), 126.47 (t), 123.31 (d), 116.41 (d), 100.57 (d), 110.30 (d). Analysis calculated for C$_{16}$H$_{13}$N$_3$O requires: C, 73.0; H, 5.0; N, 16.0%. Found: C, 72.9; H, 5.2; N, 15.9%.

Example 26

5-(Hydroxymethyl)-1-phenylbenzimidazole by the Method of Scheme 3

A solution of DIBAL (1 M in CH$_2$Cl$_2$; 1.3 mL, 1.3 mmol) was added to a solution of methyl 1-phenylbenzimidazole-5-carboxylate (Example 17) (0.15 g, 0.59 mmol) in CH$_2$Cl$_2$ (2 mL) at −78° C. The reaction was stirred for 1.5 hours, at which time MeOH (10 mL) was added, and the reaction was allowed to warm to room temperature. Sodium tartrate was added to dissolve the solids, and the mixture was extracted several times with EtOAc. The combined organic phases were dried (MgSO$_4$), filtered, and concentrated, and the residue was recrystallized from EtOAc/hexane to give Example 26 (84 mg, 63%): mp 147–149° C.

$^1$H NMR [(CD$_3$)$_2$SO]: δ4.63 (d, J=5.8 Hz, 2 H), 5.24 (t, J=5.8 Hz, 1 H), 7.30 (d, J=8.4 Hz, 1 H), 7.4–7.5 (m, 1 H), 7.58 (d, J=8.4 Hz, 1 H), 7.6–7.7 (m, 5 H), 8.54 (s, 1 H); MS(CI) (m+1)/z 225. Analysis calculated for C$_{14}$H$_{12}$N$_2$O requires: C, 75.0; H, 5.4; N, 12.5%. Found: C, 74.7; H, 5.4; N, 12.4%.

Example 27

5-Acetoxy-1-phenylbenzimidazole by the Method of Scheme 1

Reaction of 4-acetoxy-2-aminodiphenylamine (VII: R'=4-OAc, R$^{1'}$=H) with triethyl orthoformate using a known procedure [H. J. Schaeffer, C. F. Schwender, *J. Med. Chem.*, 1974;17(1): 6–8], followed by chromatography of the product on silica gel, eluting with EtOAc/hexane (1:1), gave Example 27 (77%): mp 92–94° C. (K. Fries, *Ann.*, 1927;454: 207 reports a mp of 88° C. for Example 27).

$^1$H NMR [(CD$_3$)$_2$SO]: δ2.30 (s, 3 H), 7.10 (dd, J=2.4, 8.9 Hz, 1 H), 7.4–7.5 (m, 2 H), 7.6–7.7 (m, 5 H), 8.62 (s, 1 H); MS(CI) (m+1)/z 253. Analysis calculated for C$_{15}$H$_{12}$N$_2$O$_2$ requires: C, 71.4; H, 4.8; N, 11.1%. Found: C, 71.3; H, 4.8; N, 11.0%.

Example 28

5-Ethoxy-1-phenylbenzimidazole Hydrochloride by the Method of Scheme 3

A solution of 5-hydroxy-1-phenylbenzimidazole (Example 14) (0.12 g, 0.57 mmol) in 1:1 THF/DMF (5 mL) was added under nitrogen to a stirred suspension of NaH (16 mg of a 60% dispersion in oil, 0.68 mmol) in THF (5 mL). After 5 minutes, ethyl iodide (55 μL, 0.68 mmol) was added, and the solution was stirred at 20° C. for 2 hours, then poured into brine and extracted with diethyl ether. The ether extract was washed with 2N NaOH, then water. Evaporation of the organic layer gave a residue that was dissolved in EtOAc and percolated through a plug of silica gel to give the ether Example 28 (94 mg, 69%). HCl salt: mp (MeOH/Et$_2$O) 210–213° C.

$^1$H NMR (D$_2$O): δ9.37 (s, 1 H, H-2), 7.75–7.71 (m, 3 H, Ph), 7.68–7.65 (m, 2 H, Ph), 7.61 (d, J=9.2 Hz, 1 H, H-7), 7.38 (d, J=2.3 Hz, 1 H, H-4), 7.22 (dd, J=9.2, 2.3 Hz, 1 H, H-6), 4.21 (q, J=7.0 Hz, 2 H, OCH$_2$), 1.46 (t, J=7.0 Hz, 3 H, CH$_2$CH$_3$).

$^{13}$C NMR: δ160.63 (s), 141.72 (d), 135.87 (s), 134.57 (s), 133.34 (d), 133.14 (d), 128.55 (s), 127.28 (d), 120.11 (d), 116.73 (d), 100.66 (d), 67.98 (t), 16.55 (q). Analysis calculated for C$_{15}$H$_{14}$N$_2$O.HCl requires: C, 65.6; H, 5.5; N, 10.2%. Found: C, 65.7; H, 5.3; N, 10.0%.

Example 29

1-Phenyl-5-propoxybenzimidazole hydrochloride by the Method of Scheme 3

Reaction of 5-hydroxy-1-phenylbenzimidazole (Example 14) with propyl iodide as for Example 28 gave Example 29 (76%); mp (MeOH/Et$_2$O) 204–206° C.

$^1$H NMR (D$_2$O): δ9.38 (s, 1 H, H-2), 7.75–7.71 (m, 3 H, Ph), 7.69–7.65 (m, 2 H, Ph), 7.62 (d, J=9.2 Hz, 1 H, H-7), 7.39 (d, J =2.3 Hz, 1 H, H-4), 7.24 (dd, J=9.2, 2.3 Hz, 1 H, H-6), 4.11 (t, J=6.6 Hz, 2 H, OCH$_2$), 1.86 (txq, J=7.5, 6.6 Hz, 2 H, OCH$_2$CH$_2$CH$_3$), 1.06 (t, J=7.5 Hz, 3 H, OCH$_2$CH$_2$CH$_3$).

$^{13}$C NMR: δ160.87 (s), 141.69 (d), 135.86 (s), 134.48 (s), 133.36 (d), 133.15 (d), 128.53 (s), 127.30 (d), 120.18 (d), 116.75 (d), 100.72 (d), 73.86 (t), 24.54 (t), 12.40 (q). Analysis calculated for C$_{16}$H$_{16}$N$_2$O.HCl requires: C, 66.5; H, 5.9; N, 9.7%. Found: C, 66.3; H, 5.7; N, 9.7%.

Example 30

5-Isopropoxy-1-phenylbenzimidazole Hydrochloride by the Method of Scheme 3

Reaction of 5-hydroxy-1-phenylbenzimidazole (Example 14) with isopropyl iodide as for Example 28 gave Example 30 (66%): mp (MeOH/Et$_2$O) 210–211° C.

$^1$H NMR (D$_2$O): δ9.38 (s, 1 H, H-2), 7.76–7.71 (m, 3 H, Ph), 7.70–7.66 (m, 2 H, Ph), 7.63 (d, J=9.2 Hz, 1 H, H-7), 7.44 (d, J=2.3 Hz, 1 H, H-4), 7.24 (dd, J=9.2, 2.3 Hz, 1 H, H-6), 4.79 (sp, J=6.1 Hz, 1 H, OCH(CH$_3$)$_2$) 1.41 (d, J=6.1 Hz, 6 H, OCH(CH$_3$)$_2$).

$^{13}$C NMR: δ159.32 (s), 141.93 (d), 135.87 (s), 134.62 (s), 133.32 (d), 133.13 (d), 128.74 (s), 127.29 (d), 121.23 (d), 116.80 (d), 102.87 (d), 75.51 (d), 23.66 (q). Analysis calculated for C$_{16}$H$_{16}$N$_2$O.HCl requires: C, 66.5; H, 5.9; N, 9.7%. Found: C, 66.2; H, 6.0; N, 9.7%.

Example 31

5-Butoxy-1-phenylbenzimidazole Hydrochloride by the Method of Scheme 3

Reaction of 5-hydroxy-1-phenylbenzimidazole (Example 14) with n-butyl iodide as for Example 28 gave Example 31 (72%), mp (MeOH/EtOAc) 196–197° C.

$^1$H NMR (D$_2$O): δ9.38 (s, 1 H, H-2), 7.75–7.68 (m, 5 H, Ph), 7.65 (d, J=9.2 Hz, 1 H, H-7), 7.41 (d, J=2.2 Hz, 1 H,

H-4), 7.26 (dd, J=9.2, 2.2 Hz, 1 H, H-6), 4.16 (t, J=6.6 Hz, 2 H, OCH$_2$—), 1.82 (m, 2 H, CH$_2$), 1.50 (m, 2 H, CH$_2$), 0.97 (t, J=7.5 Hz, 3 H, CH$_3$).

$^{13}$C NMR: δ160.90 (s), 141.71 (d), 135.89 (s), 134.40 (s), 133.38 (d), 133.13 (d), 128.64 (s), 127.42 (d), 120.23 (d), 116.80 (d), 100.74 (d), 72.09 (t), 33.11 (t), 21.33 (t), 15.78 (q). Analysis calculated for C$_{17}$H$_{18}$N$_2$O.HCl.0.25H$_2$O requires: C, 66.4; H, 6.4; N, 9.1%. Found: C, 66.8; H, 6.2; N, 9.3%.

Example 32

5-Allyloxy-1-phenylbenzimidazole Hydrochloride by the Method of Scheme 3

Reaction of 5-hydroxy-1-phenylbenzimidazole (Example 14) with allyl bromide as for Example 28 gave Example 32 (88%). HCl salt: mp (MeOH/Et$_2$O) 200–202° C.

$^1$H NMR (D$_2$O): δ9.40 (s, 1 H, H-2), 7.76–7.72 (m, 3 H, Ph), 7.67–7.64 (m, 2 H, Ph), 7.59 (d, J=9.2 Hz, 1 H, H-7), 7.38 (d, J=2.3 Hz, 1 H, H-4), 7.22 (dd, J=9.2, 2.3 Hz, 1 H, H-6), 6.18–6.11 (m, 1 H, CH=CH$_2$), 5.51 (dd, J17.3, 1.4 Hz, 1 H, CH=CHH), 5.42 (dd, J=10.8, 1.4 Hz, 1 H, CH=CHH), 4.69 (d, J=5.4 Hz, 2 H, OCH$_2$).

$^{13}$C NMR: δ160.22 (s), 141.79 (d), 135.77 (s), 135.04 (d), 134.45 (s), 133.34 (d), 133.15 (d), 128.53 (s), 127.16 (d), 121.48 (t), 120.19 (d), 116.73 (d), 101.08 (d), 72.57 (t). Analysis calculated for C$_{16}$H$_{14}$N$_2$O.HCl requires: C, 67.0; H, 5.3; N, 9.8%. Found: C, 67.1; H, 5.5; N, 9.8%.

Example 33

5-(2,3-Dihydroxypropoxy)-1-phenylbenzimidazole Hydrochloride by the Method of Scheme 3

Saturated aqueous KMnO$_4$ solution was added in portions over 3 hours at 20° C. to a stirred solution of 5-allyloxy-1-phenylbenzimidazole (Example 32) (0.25 g, 1.00 mmol) in acetone (50 mL) until no starting material remained. The mixture was filtered through Celite, washing with more acetone, and the filtrate was concentrated to dryness under reduced pressure. The residue was partitioned between EtOAc and water, and the organic portion was worked up and chromatographed on silica gel. EtOAc eluted foreruns while MeOH/EtOAc (1:19) gave the diol Example 33 (0.18 g, 63%). HCl salt: mp (MeOH/Et$_2$O) 182–183° C.

$^1$H NMR (D$_2$O): δ9.35 (s, 1 H, H-2), 7.75–7.68 (m, 5 H, Ph), 7.66 (d, J=9.3 Hz, 1 H, H-7), 7.42 (d, J=2.2 Hz, 1 H, H-4), 7.30 (dd, J=9.3, 2.2 Hz, 1 H, H-6 ), 4.27–4.22 (m, 1 H, CHOH), 4.20–4.14 (m, 2 H, ArOCH$_2$), 3.84–3.74 (m, 2 H, CH$_2$OH).

$^{13}$C NMR: δ160.68 (s), 141.95 (d), 135.96 (s), 134.70 (s), 133.31 (d), 133.12 (d), 128.92 (s), 127.40 (d), 120.10 (d), 116.80 (d), 100.87 (d), 72.70 (d), 72.48 (t), 65.03 (t). Analysis calculated for C$_{16}$H$_{16}$N$_2$O$_3$.HCl.0.5H$_2$O requires: C, 58.2; H, 5.5; N, 8.5%. Found: C, 58.0; H, 5.0; N, 8.8%.

Example 34

5-(2,3-Epoxypropoxy)-1-phenylbenzimidazole by the Method of Scheme 3

A solution of 5-hydroxy-1-phenylbenzimidazole (Example 14) (0.24 g, 1.14 mmol) 1:1 THF/DMF (5 mL) was added under nitrogen to a stirred suspension of sodium hydride (41 mg of a 60% dispersion in oil, 1.71 mmol). After 5 minutes, epichlorohydrin (98 μL, 1.26 mmol) was added, and the solution was refluxed for 4 hours. The cooled solution was partitioned between diethyl ether and water, and the extract was washed with 2N NaOH and worked up to give an oil which was chromatographed on silica gel. EtOAc/petroleum ether (1:1) eluted foreruns, while EtOAc eluted the epoxide Example 34 (0.14 g, 46%): mp (EtOAc/petroleum ether) 96–97.5° C.

$^1$H NMR (CDCl$_3$): δ8.06 (s, 1 H, H-2), 7.59–7.43 (m, 5 H, Ph), 7.43 (d, J=8.7 Hz, 1 H, H-7), 7.34 (d, J=2.4 Hz, 1 H, H-4), 7.02 (dd, J=8.7, 2.4 Hz, 1 H, H-6), 4.32 (dd, J=10.9, 3.1 Hz, 1 H, ArOCHH), 4.04 (dd, J=10.9, 5.7 Hz, 1 H, ArOCHH), 3.44–3.40 (m, 1 H, CHO), 2.94 (dd, J=4.9, 4.3 Hz, 1 H, CHHO), 2.81 (dd, J=4.9, 2.6 Hz, 1 H, CHHO).

$^{13}$C NMR: δ155.29 (s), 144.84 (s), 142.51 (d), 136.38 (s), 130.04 (d), 128.64 (s), 127.94 (d), 123.79 (d), 114.28 (d), 110.99 (d), 103.67 (d), 69.44 (t), 50.17 (d), 44.77 (t). Analysis calculated for C$_{15}$H$_{14}$N$_2$O$_2$ requires: C, 72.2; H, 5.3; N, 10.5%. Found: C, 71.8; H, 4.8; N, 10.6%.

Example 35

5-(2-Aminoethoxy)-1-phenylbenzimidazole Dihydrochloride by the Method of Scheme 3

A solution of 5-hydroxy-1-phenylbenzimidazole (Example 14) (0.10 g, 0.47 mmol) in 1:1 THF/DMF (2 mL) was added under nitrogen to a stirred suspension of sodium hydride (28.5 mg of a 60% dispersion in oil, 1.19 mmol) in THF (4 mL). After 10 minutes, solid 2-bromoethylamine hydrobromide (97 mg, 0.47 mmol) was added, and the mixture was warmed at 45° C. for 30 minutes. A further portion of sodium hydride (28.5 mg) followed by bromoethylamine hydrobromide (97 mg) was added and stirring was continued at this temperature for 1 hour. Water was added, followed by brine, and the mixture was extracted into EtOAc. The organic solution was extracted into 2N HCl, and the extract was basified with 2N NaOH, extracted into ether, and the ether solution worked up to give an oil which was chromatographed on alumina. EtOAc eluted foreruns while MeOH/EtOAc (1:9) gave the product Example 35 as a solid (68.5 mg, 58%). DiHCl salt: mp (MeOH/Et$_2$O) 252–254° C.

$^1$ H NMR (D$_2$O): δ9.43 (s, 1 H, H-2), 7.78–7.72 (m, 6 H, Ph and H-7), 7.51 (d, J=2.3 Hz, 1 H, H-4), 7.38 (dd, J=9.2, 2.3 Hz, 1 H, H-6), 4.46 (t, J=4.9 Hz, 2 H, CH$_2$NH$_3$), 3.56 (t, J=4.9 Hz, 2 H, OCH$_2$).

$^{13}$C NMR: δ160.02 (s), 142.22 (d), 135.96 (s), 134.61 (s), 133.40 (d), 133.16 (d), 129.29 (s), 127.54 (d), 120.04 (d), 117.02 (d), 100.97 (d), 67.55 (t), 41.64 (t). Analysis calculated for C$_{15}$H$_{15}$N$_3$O.2HCl.0.5H$_2$O requires: C, 53.7; H, 5.4; N, 12.5%. Found: C, 53.8; H, 5.5; N, 12.5%.

Example 36

5-[2-(N,N-Dimethylamino)ethoxy]-1-phenylbenzimidazole Dihydrochloride by the Method of Scheme 3

Similar reaction of 5-hydroxy-1-phenylbenzimidazole (Example 14) with sodium hydride followed by 2-dimethylaminoethyl chloride hydrochloride gave Example 36 (47%). DiHCl salt: mp (MeOH/Et$_2$O) 205–207° C. (hygroscopic foam).

$^1$H NMR (D$_2$O): δ9.45 (s, 1 H, H-2), 7.77–7.72 (m, 6 H, Ph and H-7), 7.53 (d, J=2.3 Hz, 1 H, H-4),7.39 (dd, J=9.2, 2.3 Hz, 1 H, H-6),4.55 (t, J=5.0 Hz, 2 H, CH$_2$N$^+$Me$_2$), 3.73 (t, J=5.0 Hz, 2 H, OCH$_2$). 3.06 (s, 6 H, N$^+$Me$_2$).

$^{13}$C NMR: δ159.71 (s), 142.27 (d), 135.91 (s), 134.42 (s), 133.43 (d), 133.15 (d), 129.39 (s), 127.57 (d), 119.97 (d), 117.08 (d), 100.98 (d), 65.16 (t), 58.91 (t), 45.63 (q). Analysis calculated for $C_{17}H_{19}N_3O \cdot 2HCl$ requires: C, 57.5; H, 6.0; N, 11.9%. Found: C, 57.4; H, 6.1; N, 11.8%.

Example 37

5-[3--(N,N-Dimethylamino)propoxyl]-1-phenylbenzimidazole Dihydrochloride by the Method of Scheme 3

Similar reaction of 5-hydroxy-1-phenylbenzimidazole (Example 14) with sodium hydride followed by 3-dimethylaminopropyl chloride hydrochloride gave Example 37 (52%). DiHCl salt: mp (MeOH/Et$_2$O) dec. above 76° C. (hygroscopic).

$^1$H NMR (D$_2$O): δ9.41 (s, 1 H, H-2), 7.75–7.71 (m, 6 H, Ph and H-7), 7.46 (d, J=2.3 Hz, 1 H, H-4), 7.33 (dd, J=9.2, 2.3 Hz, 1 H, H-6), 4.30 (t, J=5.7 Hz, 2 H, CH$_2$ N$^+$Me$_2$), 3.44 (t, J=7.7 Hz, 2 H, CH$_2$O), 2.98 (s, 6 H, N$^+$Me$_2$), 2.36–2.29 (m, 2 H, CH$_2$CH$_2$CH$_2$).

$^{13}$C NMR: δ160.49 (s), 142.01 (d), 135.94 (s), 134.43 (s), 133.42 (d), 133.14 (d), 129.08 (s), 127.58 (d), 120.15 (d), 116.97 (d), 100.76 (d), 68.73 (t), 58.21 (t), 45.63 (q), 26.69 (t). Analysis calculated for $C_{18}H_{21}N_3O \cdot 2HCl \cdot 3.5H_2O$ requires: C, 50.1; H, 7.0; N, 9.7%. Found: C, 50.2; H, 7.2; N, 9.8%.

Example 38

5-[2-(4-Morpholino)ethoxy]-1-phenylbenzimidazole Dihydrochloride by the Method of Scheme 3

Similar reaction of 5-hydroxy-1-phenylbenzimidazole (Example 14) with sodium hydride followed by 4-(2-chloroethyl)morpholine hydrochloride gave Example 38 (57%). DiHCl salt: mp (MeOH/Et$_2$O) 232–234° C. (hygroscopic foam).

$^1$H NMR (D$_2$O): δ9.44 (s, 1 H, H-2), 7.78–7.72 (m, 6 H, Ph and H-7), 7.53 (d, J=2.3 Hz, 1 H, H-4), 7.39 (dd, J=9.2, 2.3 Hz, 1 H, H-6), 4.60 (t, J4.8 Hz, 2 H, CH$_2$N$^+$), 4.19–3.95 (2×br, 4 H, morpholino CH$_2$N$^+$), 3.79 (t, J=4.8 Hz, 2 H, CH$_2$O).

$^{13}$C NMR: δ159.61 (s), 142.34 (d), 135.95 (s), 134.60 (s), 133.40 (d), 133.16 (d), 129.42 (s), 127.55 (d), 119.93 (d), 117.07 (d), 101.05 (d), 66.38 (t), 64.70 (t), 58.57 (t), 54.73 (t). Analysis calculated for $C_{19}H_{21}N_3O_2 \cdot 2HCl \cdot 0.5H_2O$ requires: C, 56.3; H, 6.0, N, 10.4%. Found: C, 56.4; H, 6.2; N, 10.2%.

Example 39

5-[3-(4-Morpholino)propoxy]-1-phenylbenzimidazole Dihydrochloride by the Method of Scheme 3

Similar reaction of 5-hydroxy-1-phenylbenzimidazole (Example 14) with sodium hydride followed by 4-(3-chloropropyl)morpholine hydrochloride gave Example 39 (52%). DiHCl salt: mp (MeOH/Et$_2$O) dec. above 84° C. (hygroscopic solid).

$^1$H NMR (D$_2$O): δ9.42 (s, 1 H, H-2), 7.81–7.74 (m, 5 H, Ph), 7.72 (d, J=9.2 Hz, 1 H, H-7), 7.47 (d, J=2.2 Hz, 1 H, H-4), 7.34 (dd, J=9.2, 2.2 Hz, 1 H, H-6), 4.33 (t, J=5.6 Hz, 2 H, CH$_2$N$^+$), 4.23 (br d, J=12.9 Hz, 2 H, morpholino CH$_2$N$^+$), 3.92 (br t, J=12.9 Hz, 2 H, morpholino CH$_2$N$^+$), 3.70 (br d, J=12.6 Hz, 2 H, morpholino CH$_2$O), 3.52 (t, J=5.6 Hz, 2 H, CH$_2$O), 3.36–3.28 (m, 2 H, morpholino CH$_2$O), 2.42–2.36 (m, 2 H, CH$_2$CH$_2$CH$_2$).

$^{13}$C NMR: δ160.39 (s), 142.00 (d), 135.93 (s), 134.61 (s), 133.35 (d), 133.14 (d), 128.94 (s), 127.43 (d), 120.08 (d), 116.89 (d), 100.79 (d), 68.65 (t), 66.58 (t), 57.58 (t), 54.62 (t), 25.86 (t). Analysis calculated for $C_{20}H_{23}N_3O_2 \cdot 2HCl \cdot 3.5H_2O$ requires: C, 50.7; H, 6.7; N, 8.9%. Found: C, 51.1; H, 7.0; N, 8.8%.

Example 40

6-Methoxy-1-phenylbenzimidazole by the Method of Scheme 1

Sodium methoxide (4.4 mL of a 4 M solution in MeOH) was added to a solution of 5-chloro-2-nitrodiphenylamine (VI, R'=5-Cl, R$^{1'}$=H) (2.0 g, 8.0 mmol) in MeOH (25 mL). The reaction was heated at reflux for 48 hours and cooled to room temperature, and the precipitate of 5-methoxy-2-nitrodiphenylamine (VI, R'=5-OCH$_3$, R$^{1'}$=H) was collected by filtration, washed with water and dried (1.9 g, 99%); mp (MeOH) 108–110° C.

$^1$H NMR [(CD$_3$)$_2$SO]: δ3.73 (s, 3 H), 6.49 (dd, J=2.4, 9.6 Hz, 1 H), 6.53 (d, J=2.4Hz, 1 H), 7.24 (t, J=7.2Hz, 1 H), 7.3–7.5 (m, 4 H), 8.13 (d, J=9.6 Hz, 1 H), 9.65 (s, 1 H); MS(CI) (m+1)/z245. Analysis calculated for $C_{13}H_{12}N_2O_3$ requires: C, 63.9; H, 4.9; N, 11.5%. Found: C, 63.8; H, 4.9; N, 11.4%.

A solution of this (1.5 g, 6.15 mmol) in MeOH/THF (1:1, 100 mL) was hydrogenated over 5% Pd—C for 15 hours, then filtered and concentrated. The residue was chromatographed on silica gel, eluting with EtOAc/hexane (1:2), to give 5-methoxy-2-aminodiphenylamine (1.05 g, 79%), which was used directly. Reaction with formic acid followed by chromatography on silica gel and elution with EtOAc/hexane (1:1), gave Example 40 (73%); mp 71–73° C. (Y. S. Tsizin and S. A. Chemyak, *Khim. Geterotsikl. Soedin.,* 1978;12: 1680–1683; CA 90: 137728 have reported the synthesis of Example 40).

$^1$H NMR [(CD$_3$)$_2$SO]: δ3.80 (s, 3 H), 6.93 (dd, J=2.4, 8.7 Hz, 1 H), 7.06 d, J=2.4 Hz, 1 H), 7.45–7.55 (m, 1 H), 7.6–7.7 (m, 5 H), 8.41 (s, 1 H); MS(CI) (m+1)/z225. Analysis calculated for $C_{14}H_{12}N_2O$ requires: C, 75.0; H, 5.4; N, 12.5%. Found: C, 74.9; H, 5.5; N, 12.4%.

Example 41

6-Hydroxy-1-phenylbenzimidazole Hydrochloride by the Method of Scheme 3

Reaction of the methyl ether (Example 40) with HBr in glacial acetic acid, as described above for the ether Example 2 gave the phenol (Example 41) as the hydrochloride salt (88%): mp 210–212° C. (Y. S. Tsizin and S. A. Chernyak, *Khim. Geterotsikl. Soedin.,* 1978;12: 1680–1683; CA 90: 137728 have reported the synthesis of Example 41).

$^1$H NMR (D$_2$O): δ9.34 (s, 1 H, H-2), 7.74–7.70 (m, 4 H, Ph and H-4), 7.61–7.58 (m, 2 H, Ph), 7.16 (dd, J=9.1, 2.2 Hz, 1 H, H-5), 6.92 (d, J=2.2 Hz, 1 H, H-7).

$^{13}$C NMR: δ158.22 (s), 141.50 (d), 135.67 (s), 134.77 (s), 133.20 (d), 133.10 (d), 127.25 (s), 127.03 (d), 119.65 (d), 118.54 (d), 100.22 (d).

Example 42

6-Chloro-1-phenylbenzimidazole was prepared by the method of F. Montanari and R. Passerini, *Boll. sci. facolta chim. ind. Bologna,* 1953;11: 42–45; CA 48: 6436b.

Example 43

Methyl 1-phenylbenzimidazole-6-carboxylate Hydrochloride by the Method of Scheme 3

A mixture of 1-phenylbenzimidazole-6-carboxylic acid hydrochloride (0.50 g, 2.10 mmol) and SOCl$_2$ (10 mL) in 1,2-dichloroethane (50 mL) containing DMF (1 drop) was refluxed for 2 hours. The solution was concentrated to dryness under reduced pressure. The resulting crude acid chloride was dissolved in methanol (20 mL) and the solution refluxed for 15 minutes. The methanol was removed under reduced pressure and the residue partitioned between EtOAc and saturated aqueous $NaHCO_3$. The organic solution was worked up to give Example 43 (0.48 g, 91%) as the hydrochloride salt: mp ($MeOH/Et_2O$) 200–203° C.

$^1H$ NMR ($D_2O$): δ9.68 (s, 1 H, H-2), 8.35 (br s, 1 H, H-7), 8.30 (br d, J=8.7 Hz, 1 H, H-5), 8.02 (d, J=8.7 Hz, 1 H, H-4), 7.74 (br s, 5 H, Ph), 3.95 (s, 3 H, $COOCH_3$).

$^{13}C$ NMR: δ170.47 (s), 145.03 (d), 136.46 (s), 135.40 (s), 134.11 (s), 133.75 (d), 133.25 (d), 131.31 (s), 130.74 (d), 127.72 (d), 118.03 (d), 118.01 (d), 55.79 (q). Analysis calculated for $C_{15}H_{12}N_2O_2 \cdot HCl$ requires: C, 62.4; H, 4.5; N, 9.7%. Found: C, 62.6; H, 4.4; N, 9.8%.

Example 44

6-Ethoxy-1-phenylbenzimidazole by the Method of Scheme 1

Sodium ethoxide (17.7 mL of a 1 M solution) was added to a solution of 5-chloro-2-nitrodiphenylamine (VI: R'=5-Cl, $R^{1'}$=H) (2.0 g, 8.0 mmol) in MeOH (5 mL). The reaction was heated at reflux for 48 hours, then the reaction was cooled to room temperature and filtered to collect 5-ethoxy-2-nitrodiphenylamine (VI: R'=5-OEt, $R^{1'}$=H) (1.0 g, 50%): mp (EtOH) 101–102° C.

$^1H$ NMR [$(CD_3)_2SO$]: δ1.27 (t, J=7.0 Hz, 3 H), 3.98 (q, J=7.0 Hz, 2 H), 6.4–6.5 (m, 2 H), 7.24 (t, J=7.2 Hz, 1 H), 7.3–7.5 (m, 4 H), 8.1–8.2 (m, 1 H), 9.63 (s, 1 H); MS(CI) (m+1)/z259. Analysis calculated for $C_{14}H_{14}N_2O_3$ requires: C, 65.1; H, 5.5; N, 10.9%. Found: C, 64.9; H, 5.5; N, 10.9%.

Reduction of the 5-ethoxydiphenylamine with Raney nickel as above, using EtOH/THF (1:1), gave 5-ethoxy-2-aminodiphenylamine (VII: R'=5-OEt, $R^{1'}$=H) (92%), which was used directly.

$^1H$ NMR [$(CD_3)_2SO$]: δ1.25 (t, J=7.0 Hz, 3 H), 3.84 (q, J=7.0 Hz, 2 H), 4.32 (s, 2 H), 6.43 (dd, J=2.7, 8.5 Hz, 1 H), 6.60 (d, J=2.7 Hz, 1 H), 6.65 (d, J=8.5 Hz, 1 H), 6.69 (t, J=7.23 Hz, 1 H), 6.78 (d, J=7.7 Hz, 2 H), 7.1–7.2 (m, 3 H); MS(CI) (m+1)/z229.

Reaction of the above aminodiphenylamine with formic acid, followed by chromatography of the product on silica gel, eluting with EtOAc/hexane (1:1), gave Example 44 (82%): mp 66–69° C. (Jacobson, W. Fischer, Chem. Ber., 1892;25: 1000 report a mp of 77–78° C. for Example 44).

$^1H$ NMR [$(CD_3)_2SO$]: δ1.33 (t, J=7.0 Hz, 3 H), 4.04 (d, J=7.0 Hz, 2 H), 6.92 (dd, J=2.4, 8.9 Hz, 1 H), 7.04 (d, J=2.2 Hz, 1 H), 7.4–7.5 (m, 1H), 7.6–7.7 (m, 5 H), 8.41 (s, 1 H); MS(CI) (m+1)/z239. Analysis calculated for $C_{15}H_{14}N_2O$ requires: C, 75.6; H, 5.9; N, 11.8%. Found: C, 75.7; H, 6.0; N, 11.7%.

Example 45

1-(4-Aminophenyl)-5-methoxybenzimidazole Dihydrochloride by the Method of Scheme 1

A mixture of 4-methoxy-2-nitroaniline (IV: R'=4-OMe) (1.00 g, 5.95 mmol), $K_2CO_3$ (0.34 g, 2.46 mmol), CuI (50 mg) and 4-nitrobromobenzene (V: $R^{1'}$=4-$NO_2$) (3.00 g, 0.015 mol) was heated with stirring to 150° C. and held at this temperature for 48 hours. The cooled mixture was partitioned between EtOAc and brine, and the organic portion was worked up and columned on silica gel. EtOAc/petroleum ether (1:1) eluted the diphenylamine (VI: R'=4-OMe, $R^{1'}$=4-$NO_2$) and a little of the starting methoxynitroaniline as an inseparable mixture (1.12 g) which was used directly. The mixture was dissolved in EtOAc/MeOH (1:1) (50 mL) and hydrogenated over 5% Pd—C (0.20 g) for 3 hours. After removal of the catalyst by filtration through Celite, the solvent was removed under reduced pressure, and the residue was dissolved in 4N HCl (30 mL) containing formic acid (1 mL) and the solution refluxed for 90 minutes. After concentration to dryness, the residue was basified with 2N $NH_4OH$ solution and extracted into EtOAc. Workup gave an oily solid which was chromatographed on silica gel. EtOAc/petroleum ether (1:1) eluted foreruns while EtOAc gave (Example 45) (0.26 g, 17%). DiHCl salt: mp (MeOH/$Et_2O$) 237–239° C.

$^1H$ NMR ($D_2O$): δ9.44 (s, 1 H, H-2), 7.86 (d, J=8.7 Hz, 2 H, H-3'5'), 7.70 (d, J=9.2 Hz, 1 H, 7), 7.69 (d, J=8.7Hz, 2 H, H-2', 6'), 7.46 (d, J=2.3 Hz, 1 H, H-4), 7.33 (dd, J=9.2, 2.3 Hz, 1 H, H-6), 3.98 (s, 3 H, $OCH_3$).

$^{13}C$ NMR δ161.69 (s), 142.02 (d), 137.08 (s), 135.28 (s), 134.53 (s), 129.41 (d), 128.71 (s), 126.89 (d), 120.08 (d), 116.64 (d), 99.97 (d), 58.90 (q). Analysis calculated for $C_{14}H_{13}N_3O \cdot 2HCl \cdot 0.5H_2O$ requires: C, 52.3; H, 5.0; N, 13.1%. Found: C, 52.0; H, 5.0; N, 12.6%.

Example 46

5,6-Dimethoxy-1-phenylbenzimidazole Hydrochloride by the Method of Scheme 1

A mixture of 1-bromo-4,5-dimethoxy-2-nitrobenzene (II: R'4,5-diOMe, halogen=Br) (1.00 g, 4.34 mmol), $K_2CO_3$ (1.20 g, 8.70 mmol), CuI (100 mg) and aniline (III: $R^{1'}$=H) (5 mL) was refluxed under nitrogen for 5 hours. After diluting with excess 3N HCl, the mixture was extracted with EtOAc and worked up to give an oil which was chromatographed on silica gel. EtOAc/petroleum ether (1:5) eluted 4,5-dimethoxy-2-nitrodiphenylamine (VI: R'=4,5-diOMe, $R^{1'}$=H) (0.63 g, 60%): mp (MeOH) 120–122° C.

$^1H$ NMR: δ($CDCl_2$) 9.87 (br, 1 H, NH), 7.64 (s, 1 H, H-6), 7.45–7.42 (m. 2 H, Ph), 7.32–7.22 (m, 3 H, Ph), 6.63 (s, 1 H, H-3), 3.90, 3.78 (2s, 6 H, $OCH_3$). Analysis required for $C_{14}H_{14}N_2O_4 \cdot 0.5H_2O$ requires: C, 59.4; H, 5.3; N, 9.9%. Found: C, 59.8; H, 5.3; N, 9.8%.

Hydrogenation of the above diphenylamine followed by reaction with formamidine acetate gave Example 46 (79%). HCl salt: mp (MeOH/Et2O) 217–218.5° C. (P. Jacobson, M. Jaenicke and F. Meyer, Ber., 1896;29: 2680–2690 report a mp of 106–107° C. for the free base form of Example 46).

$^1H$ NMR ($D_2O$): δ9.26 (s, 1 H, H-2), 7.77–7.72 (m, 3 H, Ph), 7.69–7.64 (m, 2 H, Ph), 7.37 (s, 1 H, H-4), 7.07 (s, 1 H, H-7), 3.95–3.83 (2s, 6 H, $OCH_3$).

$^{13}$CNMR: δ152.13 (2s), 140.18 (d), 135.95 (s), 133.39 (d), 133.23 (d), 128.31 (s), 127.66 (s), 127.42 (d), 99.13 (d), 97.27 (d), 59.00 (q), 58.91 (q). Analysis calculated for $C_{15}H_{14}N_2O_2 \cdot HCl$ requires: C, 62.0; H, 5.2; N, 9.6%. Found: C, 61.4; H, 5.3; N, 9.5%.

Example 47

5,6-Dihydroxy-1-phenylbenzimidazole Hydrochloride by the Method of Scheme 3

A mixture of the free base of Example 46 (0.80 g, 3.15 mmol) and freshly prepared pyridine hydrochloride (20 g) was warmed to 220° C. under a stream of nitrogen. After 1 hour at this temperature, the cooled mixture was diluted with water, basified with 2N NaOH, and washed well with diethyl ether. The aqueous portion was carefully neutralized with 3N HCl, extracted with EtOAc, and worked up to give an oil which was chromatographed on silica gel. EtOAc eluted foreruns while MeOH/EtOAc (1:15) gave Example 47 (0.54 g, 76%). HCl salt: mp (MeOH/Et$_2$O) 239–242° C.

$^1$H NMR (D$_2$O): δ9.16 (s, 1 H, H-2), 7.73–7.68 (m, 3 H, Ph), 7.66–7.62 (m, 2 H, Ph), 7.27 (s, 1 H, H-4), 7.08 (s, 1 H, H-7).

$^{13}$C NMR: δ148.46 (s), 148.43 (s), 140.09 (d), 136.12 (s), 133.17 (d), 133.10 (d), 128.35 (s), 127.54 (s), 127.34 (d), 102.43 (d), 100.83 (d). Analysis calculated for C$_{13}$H$_{10}$N$_2$O$_2$.HCl.1.5H$_2$O requires: C, 53.9; H, 4.9; N, 9.7%. Found: C, 53.8; H, 4.6; N, 9.5%.

Example 48

5,6-Methylenedioxy-1-phenylbenzimidazole Hydrochloride by the Method of Scheme 3

A mixture of the benzimidazole Example 47 (0.20 g, 0.88 mmol), 50% aqueous NaOH solution (8 mL), tetrabutylammonium bromide (40 mg, 0.12 mmol) and dibromomethane (8 mL) was refluxed for 3 hours. After dilution with CH$_2$Cl$_2$, the organic portion was worked up to give an oil which was chromatographed on silica gel. EtOAc/petroleum ether (1:1) eluted Example 48 (0.16 g, 75%). HCl salt: mp (MeOH/Et$_2$O) 239–241° C.

$^1$H NMR (D$_2$O): δ9.21 (s, 1 H, H-2), 7.73–7.69 (m, 3 H, Ph), 7.67–7.63 (m, 2 H, Ph), 7.30 (s, 1 H, H-4), 7.14 (s, 1 H, H-7), 6.15 (s, 2 H, OCH$_2$O).

$^{13}$C NMR: δ151.12 (s), 151.03 (s), 140.30 (d), 135.97 (s), 133.35 (d), 133.12 (d), 129.61 (s), 128.69 (s), 127.55 (d), 105.63 (t), 96.94 (d), 95.53 (d). Analysis calculated for C$_{14}$H$_{10}$N$_2$O$_2$.HCl.0.25H$_2$O requires: C, 60.2; H, 4.2; N, 10.0%. Found: C, 60.0; H, 4.2; N, 10.1%.

Example 49

5-Methoxy-6-methyl-1-phenylbenzimidazole Hydrochloride by the Method of Scheme 1

A mixture of 4-methoxy-5-methyl-2-nitroaniline (IV: R'=4-OMe, 5-Me) (1.00 g, 5.49 mmol), K$_2$CO$_3$ (0.50 g, 3.62 mmol), CuI (100 mg) and bromobenzene (V: R$^1$=H) (5 mL) was refluxed under nitrogen with stirring for 4 days. The mixture was concentrated to dryness under reduced pressure, and the residue was partitioned between EtOAc and water and filtered through Celite. The organic layer was worked up to give an oil which was chromatographed on silica gel. Petroleum ether eluted foreruns, while EtOAc/petroleum ether (1:9) gave 4-methoxy-5-methyl-2-nitrodiphenylamine (VI: R'=4-OMe, 5-Me, R$^1$=H) (1.26 g, 88%): mp (MeOH at –20° C.) 94–96° C.

$^1$H NMR (CDCl$_3$): δ9.46 (brs, 1 H, NH), 7.55 (s, 1 H, H-3), 7.42–7.38 (m, 2 H, Ph), 7.26–7.24 (m, 2 H, Ph), 7.22–7.18 (m, 1 H, Ph), 6.98 (d, J=0.7 Hz, 1 H, H-6), 3.84 (s, 3 H, OCH$_3$), 2.17 (s, 3 H, CH$_3$).

$^{13}$C NMR: δ149.95 (s), 139.34 (s), 138.78 (s), 138.04 (s), 129.65 (d), 124.99 (d), 123.71 (d), 117.70 (d), 104.92(d), 55.77 (q), 17.0 5 (q). Analysis calculated for C$_{14}$H$_{14}$N$_2$O$_3$ requires: C, 65.1; H, 5.5; N, 10.8%. Found: C, 65.1; H, 5.4; N, 10.8%.

Hydrogenation of the above diphenylamine, followed by reaction with formamidine acetate, gave Example 49 (7(1%) HCl salt: mp (MeOH/Et$_2$O) 214–2175C.

$^1$H NMR (D$_2$O): δ9.26 (s, 1 H, H-2), 7.73–7.70 (m, 3 H, Ph), 7.63–7.60 (m Ph), 7.45 (s, 1 H, H-7), 7.3 1 (s, 1 H, H-4), 3.96 (s, 3 H, OCH$_3$), 2.27 (s, 3 H, 3CH$_3$).

$^{13}$C NMR: δ160.20 (s), 140.38 (d), 135.91 (s), 133.21 (d), 133.08 (d), 132.73 (s), 131.48(s), 12 7.86(s), 127.14 (d), 116.15 (d), 97.82 (d), 58.79 (q), 19.08 (q). Analysis calculated for C$_{15}$H$_{14}$N$_2$O.HCl.0 .25H$_2$O requires: C, 64.5; H, 5.6; N, 10.0%. Found: C, 64.4; H, 5.5; N, 10.2%.

Example 50

5-Hydroxy-6-methyl-1-phenylbenzimidazole Hydrochloride by the Method of Scheme 3

Demethylation of the ether Example 49 using HBr in acetic acid as described for synthesis of Example 2 gave Example 50 (82%). HCl salt: mp (MeOH/Et$_2$O) 239–243° C.

$^1$H NMR (D2O): δ9.24 (s, 1 H, H-2), 7.74–7.70 (m, 3 H, Ph), 7.66–7.63 (m, 2 H, Ph), 7.49 (s, 1 H, H-7), 7.23 (s, 1 H, H-4), 2.30 (s, 3 H, CH$_3$).

$^{13}$C NMR: δ156.80 (s), 140.69 (d), 136.01 (s), 133.25 (d), 133.08 (d), 132.55 (s), 130.31 (s), 128.23 (s), 127.38 (d), 116.65 (d), 101.36 (d), 18.99 (q). Analysis calculated for C$_{14}$H$_{12}$N$_2$O.HCl requires: C, 64.5; H, 5.0; N, 10.7%. Found: C, 64.2; H, 4.9; N, 10.7%.

Example 51

Methyl 5-methoxy-1-phenylbenzimidazole-6-carboxylate Hydrochloride by the Method of Scheme 3

Treatment of 5-methoxy-1-phenylbenzimidazole-6-carboxylic acid hydrochloride with thionyl chloride followed by MeOH, as described for the synthesis of Example 43, gave Example 51 (91%). HCl salt: mp (MeOH/Et$_2$O) 203–205° C.

$^1$H NMR (D$_2$O): δ9.44 (s, 1 H, H-2), 7.95 (s, 1 H, H-7), 7.73–7.69 (m, 3 H, Ph), 7.62–7.59 (m, 2 H, Ph), 7.46 (s, 1 H, H-4), 3.96–3.86 (2s, 6 H, OCH$_3$).

$^{13}$C NMR: δ169.72 (s), 160.51 (s), 144.52 (d), 138.12 (s), 135.50 (s), 133.44 (d), 133.22 (d), 127.53 (s), 127.02 (d), 121.74 (s), 119.16 (d), 100.68 (d), 59.30 (q). Analysis calculated for C$_{16}$H$_{14}$N$_2$O$_3$ HCl.0.5H$_2$O requires: C, 58.6; H, 4.9; N, 8.6%. Found: C, 58.7; H, 4.5; N, 8.6%.

5-Methoxy-1-phenylbenzimidazole-6-carboxylic acid hydrochloride was prepared by the method of Scheme 3 as follows: Powdered KMnO$_4$ (4.08 g, 0.026 mol) was added in portions over 12 hours to a refluxing solution of the free base of 5-methoxy-6-methyl-1-phenylbenzimidazole (Example 49) (1.50 g, 6.29 mmol) in 1:1 tert-butanol/water (600 mL), by which time no starting material was present. The hot mixture was filtered through Celite, washing through with water. The filtrate was concentrated under reduced pressure to a volume of conc. 100 mL and washed with EtOAc. The aqueous portion was carefully neutralized with 3N HCl, chilled to 5° C. for 4 hours, and the precipitated 5-methoxy-1-phenylbenzimidazole-6-carboxylic acid (1.08 g, 64%) was removed by filtration. HCl salt: mp (MeOH/Et$_2$O) 279–281 ° C.

$^1$H NMR (D$_2$O): 5 9.45 (s, 1 H, H-2), 7.99 (s, 1 H, H-7), 7.71–7.69 (m, 3 H, Ph), 7.64–7.61 (m, 2 H, Ph), 7.51 (s, 1 H, H-4), 4.00 (s, 3 H, OCH$_3$).

$^{13}$C NMR: δ171.51 (s), 160.37 (s), 144.33 (d), 137.72 (s), 135.53 (s). 133.48 (d), 133.21 (d), 127.79 (s), 127.18 (d), 122.83 (s), 119.03 (d), 100.57 (d), 59.38 (q). Analysis calculated for $C_{15}H_{12}N_2O_3 \cdot HCl \cdot 0.25H_2O$ requires: C, 58.3; H, 4.4; N, 9.1%. Found: C, 58.2; H, 4.4; N, 9.0%.

Example 52

5-Hydroxy-1-phenylbenzimidazole-6-carboxylic acid Hydrobromide by the Method of Scheme 3

A solution of 5-methoxy-1-phenylbenzimidazole-6-carboxylic acid hydrochloride (0.60 g, 2.24 mmol) in a 33% solution of HBr in glacial acetic acid (50 mL) was refluxed for 30 hours. After cooling to room temperature, the resulting precipitate of the hydrobromide salt of Example 52 was filtered off (0.51 g, 68%): mp 288–290° C. (dec.).

$^1$H NMR [$(CD_3)_2SO$]: δ9.67 (s, 1 H, H-2), 8.03 (s, 1 H, H-7), 7.82–7.80 (m, 2 H, Ph), 7.76–7.71 (m, 2 H, Ph), 7.68–7.64 (m, 1 H, Ph), 7.39 (s, 1 H, H-4), 6.00 (br, 2 H, OH).

$^{13}$C NMR: δ171.15 (s), 158.44 (s), 145.11 (d), 139.64 (s), 133.79 (s), 130.29 (d), 129.74 (d), 125.16 (s), 124,70 (d), 114.14 (d), 112.27 (s), 102.43 (d). Analysis calculated for $C_{14}H_{10}N_2O_3 \cdot HBr$ requires: C, 50.2; H, 3.3; N, 8.4%. Found: C, 49.6; H, 2.9; N, 8.0%.

Example 53

6-Hydroxymethyl-5-methoxy-1-phenylbenzimidazole Hydrochloride by the Method of Scheme 3

Borane-methyl sulfide complex (1.11 mL of 10.0N, 0.011 mol) was added dropwise at room temperature under nitrogen to a stirred solution of 5-methoxy-1-phenylbenzimidazole-6-carboxylic acid hydrochloride(1.00 g, 3.73 mmol) in THF (60 mL). After stirring at this temperature for 3 hours, the excess of reagent was destroyed by careful addition of MeOH, followed by water, and the solution was acidified with 3N HCl and stirred at room temperature for a further 30 minutes. The aqueous solution was washed with EtOAc, then basified with conc. NH$_3$ solution, extracted with EtOAc, and the organic portion worked up to give an oily solid which was chromatographed on silica gel. EtOAc eluted foreruns, while MeOH/EtOAc (1:15) eluted the alcohol Example 53 (0.77 g, 81%). HCl salt: mp (MeOH/Et$_2$O) 260° C. (dec.).

$^1$H NMR (D$_2$O): δ9.33 (s, 1 H, H-2), 7.75–7.67 (m, 5 H, Ph), 7.67 (s, 1 H, H-7), 7.42 (s, 1 H, H-4), 4.73 (s, 2 H, CH$_2$O), 3.99 (s, 3 H, OCH$_3$).

$^{13}$C NMR: δ159.85 (s), 141.41 (d), 135.94 (s), 134.25 (s), 133.31 (d), 133.14 (d), 132.85 (s), 128.05 (s), 127.34 (d), 115.28 (d), 98.60 (d), 62.38 (t), 58.86 (q). Analysis calculated for $C_{15}H_{14}N_2O_2 \cdot HCl$ requires: C, 62.0; H, 5.2; N, 9.6%. Found: C, 62.0; H, 5.2; N, 9.5%.

Example 54

5-Methoxy-1-phenylbenzimidazole-6-carboxaldehyde Hydrochloride by the Method of Scheme 3

Manganese dioxide (0.20 g, 2.30 mmol) was added in 4 portions over 8 hours to a refluxing solution of the free base of the alcohol Example 53 (0.10 g, 0.39 mmol) in EtOAc (10 mnL), and refluxing was continued for a further 10 hours. The mixture was filtered through Celite and the filtrate percolated through a short column of silica to give the aldehyde (Example 54) (0.098 g, 99%). HCl salt: mp (MeOH//Et$_2$O) 218–220° C.

$^1$H-NMR (D$_2$O): δ10.34 (s, 1 H, CHO), 9.57 (s, 1 H, H-2), 8.16 (s, 1 H, H-7), 7.73 (br s, 5 H, Ph), 7.59 (s, 1 H, H-4), 4.08 (s, 3 H, OCH$_3$).

$^{13}$C NMR: δ194.97 (d), 163.61 (s), 144.83 (d), 138.88 (s), 135.52 (s), 133.67 (d), 133.23 (d), 128.63 (s), 127.55 (d), 127.12 (s), 117.98 (d), 100.42 (d), 59.40 (q). Analysis calculated for $C_{15}H_{14}N_2O_2 \cdot HCl \cdot 0.25H_2O$ requires: C, 61.4; H, 4.6; N, 9.6%. Found: C, 61.4; H, 4.6; N, 9.6%.

Example 55

5-Methoxy-1-(2-thienyl)benzimidazole Hydrochloride by the Method of Scheme 4

A mixture of 4-methoxy-2-nitroaniline (X: R'=4-OMe) (1.00 g, 5.95 mmol), K$_2$CO$_3$ (1.00 g, 7.23 mmol), CuI (50 mg), and 2-bromothiophene (XI: 2-Br) (5 mL, 0.052 mol) was refluxed under nitrogen with stirring for 18 hours. Excess bromothiophene was removed under reduced pressure, and the residue was partitioned between EtOAc and water and filtered through Celite. The organic portion was worked up to give an oil which was chromatographed on silica gel. EtOAc/petroleum ether (1:9) eluted 4-methoxy-2-nitro-N-(2-thienyl)aniline (XII: R=4-OMe, 2-thienyl) (0.37 g, 25%): mp (aqueous EtOH) 108–110° C.

$^1$H NMR (CDCl$_3$): δ9.17 (br, 1 H, NH), 7.37 (dd, J=1.8, 1.6 Hz, 1 H), 7.15 (dd, J=5.7, 1.4 Hz, 1 H), 7.09 (d, J=1.4 Hz, 1 H), 7.08 (s, 1 H), 6.98 (dd, J=5.7, 3.6 Hz, 1 H), 6.88 (m, 1 H), 3.82 (s, 3 H, OCH$_3$).

$^{13}$C NMR: δ151.39 (s), 141.70 (s), 139.57 (s), 126.41 (d), 126.20 (d), 123.47 (d), 122.80 (d), 118.21 (s), 117.65 (d), 106.78 (d), 55.59 (q). Analysis calculated for $C_{11}H_{10}N_2O_3S$ requires: C, 52.8; H, 4.0; N, 11.2%. Found: C, 53.1;H,4.1; N, 11.3%.

Hydrogenation of the above thienylaniline over 5% Pd-C, followed by reaction with formamidine acetate, gave Example 55 (82%) as the hydrochloride salt: mp (MeOH/Et$_2$O) 169–172° C.

$^1$H NMR (D$_2$O): δ9.36 (s, 1 H, H-2), 7.68 (dd, J=1.4, 6.8 Hz, 1 H, H-5'), 7.65 (d, J=9.2 Hz, 1 H, H-7), 7.49 (dd, J=3.9, 1.4 Hz, 1 H, H-4'), 7.37 (d, J=2.3 Hz, 1 H, H-4), 7.27 (dd, J=6.8, 3.9 Hz, 1 H, H-3'), 7.25 (dd, J=9.2, 2.3 Hz, 1 H, H-6), 3.94 (s, 3 H, OCH$_3$).

$^{13}$C NMR: δ161.58(s), 143.20(d), 135.10(s), 134.57(s), 129.68(s), 129.58(d), 129.47 (d), 128.24 (d), 119.94 (d), 116.50 (d), 100.07 (d), 58.87 (q). Analysis calculated for $C_{12}H_{10}N_2OS \cdot HCl \cdot 0.5H_2O$ requires: C, 52.3; H, 4.4; N, 10.2%. Found: C, 52.2; H, 4.3; N, 10.2%.

Example 56

5-Methoxy-1-(3-thienyl)benzimidazole Hydrochloride by the Method of Scheme 4

Reaction of 4-methoxy-2-nitroaniline (X: R=4-OMe) and 3-bromothiophene (XI: R'=3-Br) as described above for Example 55, but for only 6 hours, gave 4-methoxy-2-nitro-N-(3-thienyl)aniline (XIV: R'=4-OMe, 3-thienyl) (71%): mp (EtOAc/petroleum ether) 121–123° C.

1H NMR (CDCl$_3$): δ9.31 (br, 1 H, NH), 7.63 (d, J=3.0 Hz, 1 H, H-3), 7.36 (dd, J=5.1, 3.2 Hz, 1 H, H-4'), 7.18 (d, J=9.4 Hz, 1 H, H-6), 7.09 (dd, J=9.4, 3.0 Hz, 1 H, H-5), 7.05 (dd, J=3.2, 1.4 Hz, 1 H, H-2'), 7.01 (dd, J=5.1, 1.4 Hz, 1 H, H-5'), 3.82 (s, 3 H, OCH$_3$).

$^{13}$C NMR: δ151.01 (s), 138.79 (s), 138.71 (s), 132.12 (s), 126.55 (d), 126.06 (d), 124.74 (d), 117.63 (d), 115.05 (d), 106.82 (d), 55.86 (q). Analysis calculated for $C_{11}H_{10}N_2O_3S$: C, 52.8; H, 4.0; N, 11.2%. Found: C, 52.8; H, 4.2; N, 11.1%.

Hydrogenation of the above thienylaniline over 5% Pd-C followed by reaction with formamidine acetate gave Example 56 (77%) as the hydrochloride salt: mp (MeOH/Et$_2$O) 219–221° C. (dec.).

$^1$H NMR (D$_2$O): δ9.36 (s, 1 H, H-2), 7.88 (dd, J=3.1, 1.5 Hz, 1 H, H-2'), 7.81 (dd, J=5.1, 3.1 Hz, 1 H, H-4'), 7.62 (d, J=9.2 Hz, 1 H, H-7), 7.44 (dd, J=5.1, 1.5 Hz, 1 H, H-5'), 7.32 (d, J=2.3 Hz, 1 H, H-4), 7.20 (dd, J=9.2, 2.3 Hz, 1 H, H-6), 3.93 (s, 3 H, OCH$_3$).

$^{13}$C NMR: δ161.43 (s), 141.67 (d), 134.40 (s), 133.32 (s), 131.49 (d), 128.34 (s), 125.40 (d), 123.46 (d), 119.77 (d), 116.65 (d), 99.76 (d), 58.84 (q). Analysis calculated for C$_{12}$H$_{10}$N$_2$SO.HCl requires: C, 54.0; H, 4.2; N, 10.5%. Found: C, 54.1; H, 4.2; N, 10.6%.

Example 57

5-(4-Hydroxybutoxy)-1-phenylbenzimidazole Hydrochloride by the Method of Scheme 3

A mixture of 5-hydroxy-1-phenylbenzimidazole (0.31 g, 1.47 mmol), CsCO$_3$ (0.58 g, 1.77 mmol), and 4-chlorobutanol (0.16 mL, 1.62 mmol) in DMF (10 mL) was warmed at 115° C. for 18 hours, then concentrated to dryness under reduced pressure. The residue was partitioned between EtOAc and water, then filtered, and the organic portion was worked up and chromatographed on silica gel. EtOAc eluted a trace of starting material, while MeOH/EtOAc (1:9) gave the alcohol (Example 57) (0.34 g, 82%). HCl salt: mp (MeOH/EtOAc) 205–207° C.

$^1$H NMR (D$_2$O): δ9.37 (s, 1 H, H-2), 7.76–7.67 (m, 5 H, Ph), 7.66 (d, J=9.2 Hz, 1 H, H-7), 7.41 (d, J=1.6 Hz, 1 H, H-4), 7.28 (dd, J=9.2, 1.6 Hz, 1 H, H-6), 4.19 (t, J=6.4 Hz, 2 H, CH$_2$O), 3.69 (t, J=6.5 Hz, 2 H, CH$_2$O), 1.93–1.86 (m, 2 H, CH$_2$), 1.79–1.71 (m, 2 H, CH$_2$). $^{13}$C NMR δ160.78 (s), 141.83 (d), 135.95 (s), 134.60 (s), 133.34 (d), 133.13 (d), 128.82 (s), 127.44 (d), 120.19 (d), 116.79 (d), 100.85 (d), 71.89 (t), 64.11 (t), 30.67 (t), 27.62 (t). Analysis calculated for C$_{17}$H$_{18}$N$_2$O$_2$.HCl.0.5H$_2$O requires: C, 62.3; H, 6.2; N, 8.6%. Found: C, 61.8; H, 5.8; N, 8.4%.

Example 58

5-[4-(N,N-Dimethylamino)butoxy]-1-phenylbenzimidazole Dihydrochloride by the Method of Scheme 3

Methanesulfonyl chloride (0.27 mL, 3.31 mmol) was added dropwise at 20° C. to a stirred solution of 5-(4-hydroxybutoxy)-1-phenylbenzimidazole hydrochloride (0.85 g, 3.01 mmol) and Et$_3$N (0.50 mL, 3.61 mmol) in CH$_2$Cl$_2$ (50 mL). After 5 minutes the resulting solution was evaporated to dryness under reduced pressure to give the crude mesylate. Half of this was dissolved in MeOH (20 mL) and dimethylamine (5 mL of a 40% aqueous solution), and the mixture was warmed in a pressure vessel at 80° C. for 15 hours. After concentration to dryness the residue was partitioned between EtOAc and water, and the organic portion was chromatographed on alumina. EtOAc eluted foreruns while MeOH/EtOAc (1:9) gave the dimethylamine (Example 58) (0.32 g, 65%). DiHCl salt: mp (MeOH/Et$_2$O) 88° C. (hygroscopic).

$^1$H NMR (D$_2$O): δ9.31 (s, 1 H, H-2), 7.75–7.70 (m, 5 H, Ph), 7.70 (d, J=9.2 Hz, 1 H, H-7), 7.43 (d, J=2.3 Hz, 1 H, H-4), 7.30 (dd, J=9.2, 2.3 Hz, 1 H, H-6), 4.23 (t, J=5.7 Hz, 2 H, CH$_2$O), 3.25 (t, J=7.0 Hz, 2 H, CH$_2$N$^+$), 2.91 (s, 6 H, $^+$NMe$_2$), 2.00–1.91 (m, 4 H, CH$_2$). HRMS (EI): C$_{19}$H$_{23}$N$_3$O requires: M$^+$309.1841. Found: M$^+$309.1810

Example 59

5-[4-(4-Morpholino)butoxy]-1]phenylbenzimidazole Dihydrochloride by the Method of Scheme 3

The crude mesylate prepared in Example 58 (1.5 mmol) was dissolved in morpholine (10 mL) and refluxed for 30 minutes. After removal of excess morpholine under reduced pressure, the residue was partitioned between brine and EtOAc and the organic portion was worked up and chromatographed on alumina. EtOAc eluted the morpholide (Example 59) (0.27 g, 49%). DiHCl salt: mp (MeOH/Et$_2$O) 100–103° C. (hygroscopic powder).

$^1$H NMR (D$_2$O): δ9.40 (s, 1 H, H-2), 7.75–7.72 (m, 5 H, Ph), 7.70 (d, J=9.2 Hz, 1 H, H-7), 7.45 (d, J=2.3 Hz, 1 H, H-4), 7.32 (dd, J=9.2, 2.3 Hz, 1 H, H-6), 4.24 (t, J=5.9 Hz, 2 H, CH$_2$O), 4.17 (dd, J=13.2, 3.4Hz, 2 H, CH$_2$O), 3.90–3.82 (m, 2 H, CH$_2$O), 3.61–3.59 (m, 2 H, CH$_2$N$^+$), 3.32 (t, J=6.9 Hz, 2 H, CH$_2$N$^+$), 3.28 3.21 (m, 2 H, CH$_2$N$^+$).

$^{13}$C NMR δ160.69 (s), 141.91 (d), 135.95 (s), 134.54 (s), 133.37 (d), 133.14 (d), 128.88 (s), 127.50 (d), 120.17 (d), 116.89 (d), 100.80 (d), 71.02 (t), 66.54 (t), 59.64 (t), 54.39 (t), 28.13 (t), 22.89 (t). HRMS (CI). C21H$_{26}$N$_3$O$_2$ requires: [M+H] 352.2025. Found [M+H] 352.2103.

Example 60

4,5-Dimethoxy-1-phenylbenzimidazole Hydrochloride by the Method of Scheme 1

A solution of 3,4-dimethoxy-2-nitrobenzoic acid (6.26 g, 0.027 mol), SOCl$_2$ (10.0 mL) and DMF (1 drop) in 1,2-dichloroethane (100 mL) was refluxed for 2 hours, then concentrated to dryness under reduced pressure. The resulting crude acid chloride was dissolved in acetone (50 mL), cooled to 5° C. and treated in one portion with a solution of excess sodium azide (10.0 g) in water (20 mL). After vigorous stirring for 10 minutes the mixture was poured into water (300 mL) and the resultant precipitate of acyl azide was filtered off and washed well with water. The crude solid was slurried in acetic acid (300 mL) and water (30 mL) and heated slowly to reflux. After refluxing for 2 hours the solvents were removed under reduced pressure and the residue was slurried in hot EtOH and filtered. The filtrate was concentrated to dryness and the residue was triturated in EtOAc and worked up to give 3,4-dimethoxy-2-nitroaniline (12.96 g, 55%): mp (aqueous EtOH) 65–67° C.

$^1$H NMR (CDCl$_3$) δ6.94 (d, J=9.1 Hz, 1 H, H-5), 6.49 (d, J=9.1 Hz, 1 H, H-6), 4.44 (br, 2 H, NH$_2$) 3.96, 3.82 (2 s, 6 H, OCH$_3$).

$^{13}$C NMR δ145.03 (s), 144.00 (s), 139.45 (s), 135.73 (s), 119.15 (d), 111.75 (d), 61.94 (OCH$_3$), 57.33 (OCH$_3$). Analysis calculated for C$_8$H$_{10}$N$_2$O$_4$ requires: C, 48.5; H, 5.1; N, 14.1%. Found: C, 48.8; H, 5.1; N, 13.8%.

A mixture of the above dimethoxynitroaniline (1.40 g, 7.06 mmol), K$_2$CO$_3$ (1.50 g, 0.011 mol), CuI (0.10 g) and bromobenzene (15 mL) was refluxed with vigorous stirring for 8 hours. After removal of excess bromobenzene under reduced pressure the residue was partitioned between EtOAc and water, and the organic portion was worked up to give an oil which was chromatographed on silica gel. Petroleum ether eluted a little bromobenzene while EtOAc/petroleum ether (1:9) gave 3,4-dimethoxy-2-nitrodiphenylamine (0.46 g, 24%): mp (EtOAc/petroleum ether) 68–69° C.

$^1$H NMR (CDCl$_3$) δ7.28 (m, 2 H, Ar), 7.06–6.95 (m, 5 H, Ar), 6.68 (br s, 1 H, NH), 4.00, 3.87 (2 s, 6 H, OCH$_3$).

$^{13}$C NMR δ146.99 (s), 143.30 (s), 141.61 (s), 137.40 (s), 131.47 (s), 129.48 (d), 122.36 (d), 119.19 (d), 117.12 (d), 113.70 (d), 62.09 (OCH$_3$), 56.92 (OCH$_3$). Analysis calculated for C$_{14}$H$_{14}$N$_2$O$_4$ requires: C, 61.1; H, 5.1, N, 10.2%. Found: C, 61.1; H, 5.1; N, 10.0%.

Reduction of the above diphenylamine with H$_2$/Pd—C followed by reaction of the resulting diamino compound with formamidine acetate, gave the diether (Example 60) (76%). HCl salt: mp (MeOH/Et$_2$O) 180–183° C. (dec).

$^1$H NMR (D$_2$O) δ9.37 (s, 1 H, H-2), 7.72 (m, 3 H, Ph), 7.64 (m, 2 H, Ph), 7.41 (d, J=9.1 Hz, 1 H, H-7), 7.37 (d, J=9.1 Hz, 1 H, H-6), 4.08, 4.00 (2s, 6 H, OCH$_3$).

$^{13}$C NMR δ152.62 (s), 142.77 (d), 137.88 (s), 135.85 (s), 133.26 (d), 133.13 (d), 129.82 (s), 128.86 (s), 127.09 (d), 117.20 (d), 111.09 (d), 64.50 (OCH$_3$), 59.94 (OCH$_3$). Analysis calculated for C$_{15}$H$_{14}$N$_2$O$_2$.HCl.0.5H$_2$O requires: C, 60.1; H, 5.4; N, 9.4%. Found: C, 60.3; H, 5.5; N, 9.4%.

Example 61

4,5-Dihydroxy-1-phenylbenzimidazole Hydrochloride by the Method of Scheme 3

A mixture of the free base of the diether (Example 60) (60 mg, 0.23 mmol) and lithium methanethiolate (0.20 g, 3.77 mmol) in dry DMF (10 mL) was warmed at 120° C. under an atmosphere of nitrogen for 4 hours. The cooled solution was carefully neutralised with conc. HCl then poured into brine and extracted into EtOAc. The extract was worked up and chromatographed on silica gel. EtOAc gave foreruns while MeOH/EtOAc (1:19) eluted the diphenol (Example 61) (46 mg, 88%). HCl salt: mp (MeOH/Et$_2$O) 241–244° C.

$^1$H NMR (D$_2$O) δ9.27 (s, 1 H, H-2), 7.72–7.59 (m, 5 H, Ph), 7.18 (d, J=9.0 Hz, 1 H, H-7), 7.11 (d, J=9.0Hz, 1 H, H-6).

$^{13}$C NMR δ144.99 (s), 141.76 (d), 136.08 (s), 134.41 (s), 133.16 (d), 133.07 (d), 129.60 (s), 127.28 (d), 125.89 (s), 120.01 (d), 106.96 (d). Analysis calculated for C$_{13}$H$_{10}$N$_2$O$_2$.HCl requires: C, 59.4; H, 4.2; N, 10.7%. Found: C, 59.3; H, 4.2; N, 10.7%.

Example 62

5-Hydroxy-4-methoxy-1-phenylbenzimidazole Hydrochloride by the Method of Scheme 3

Boron tribromide (1.12 mL of a 1N solution in CH$_2$Cl$_2$, 1.12 mmol) was added under nitrogen at 5° C. to a solution of the diether (Example 60) (0.24 g, 1.12 mmol) in CH$_2$Cl$_2$ (20 mL). After 1 hour at this temperature, followed by 2 hours at room temperature, 2N NaOH (10 mL) was added and the mixture was stirred for 1 hour. The aqueous layer was carefully neutralised with 2N HCl and extracted with EtOAc, and the extract was worked up and chromatographed on silica gel. Elution with EtOAc/petroleum ether (1:1) gave Example 62 (26 mg, 12%). HCl salt: mp (MeOH//t$_2$O) 220–222° C.

$^1$H NMR (CDCl$_3$) δ8.00 (s, 1 H, H-2), 7.58–7.43 (m, 5 H, Ph), 7.08 (d, J=8.7 Hz, 1 H, H-7), 6.99 (d, J=8.7 Hz, 1 H, H-6), 5.66 (br, 1 H, OH), 4.44 (s, 3 H, OCH$_3$).

$^{13}$C NMR δ142.54 (s), 141.45 (d), 136.77 (s), 136.57 (s), 136.29 (s), 135.51 (s), 130.02 (d), 128.03 (d), 124.03 (d), 112.43 (d), 103.99 (d), 61.10 (OCH$_3$). Analysis calculated for C$_{14}$H$_{12}$N$_2$O$_2$.HCl requires: C, 60.8; H, 4.7; N, 10.1%. Found: C, 61.3; H, 4.5; N, 9.5%.

Example 63

4-Hydroxy-5-methoxy-1-phenylbenzimidazole Hydrochloride by the Method of Scheme 3

Further elution with of the column chromatography in Example 62 with EtOAc gave Example 63 (0.11 g, 50%): mp (EtOAc/petroleum ether) 196–197° C.

$^1$H NMR (CDCl$_3$) δ8.16 (s, 1 H, H-2), 7.60–7.45 (m, 5 H, Ph), 7.06 (d, J=8.7 Hz, 1 H, H-7), 6.99 (d, J=8.7 Hz, 1 H, H-6), 3.98 (s, 3 H, OCH$_3$), 1.27 (br, 1 H, OH).

Analysis calculated for C$_{14}$H$_{12}$N$_2$O$_2$ requires: C, 70.0; H, 5.0; N, 11.7%. Found: C, 70.3; H, 5.2; N, 11.7%.

Example 64

4-Bromo-5-Hydroxy-1-phenylbenzimidazole Hydrochloride by the Method of Scheme 3

A solution of N-bromosuccinimide (0.72 g, 4.04 mmol) in DMF (5 mL) was added dropwise at room temperature to a solution of 5-hydroxy-1-phenylbenzimidazole (0.85 g, 4.04 mmol) in DMF (30 mL). After 1 hour the solution was diluted with aqueous NaCl and extracted into EtOAc, and the extract was worked up to give a solid which was chromatographed on silica gel. Elution with EtOAc/ petroleum ether (1:1) gave foreruns, while EtOAc eluted Example 64 (0.88 g, 75%). HCl salt: mp (MeOH/Et$_2$O) 244–246° C.

$^1$H NMR δ(free base in CDCl$_3$) 8.12 (s, 1 H, H-2), 7.60–7.56 (m, 2 H, Ph), 7.50–7.46 (m, 3 H, Ph), 7.36 (d, J=Hz, 1 H, H-7), 7.08 (d, J=8.8 Hz, 1 H, H-6), 5.85 (br, 1 H, OH).

$^{13}$C NMR δ149.30 (s), 142.88 (d), 135.91 (s), 130.14 (d), 128.44 (s), 128.41 (d), 124.11 (s), 124.03 (d), 113.18 (d), 110.33 (d), 99.66(s).

Analysis calculated for C$_{13}$H$_{19}$BrN$_2$O.HCl requires: C, 48.0; H, 3.1; N, 8.6%.

Found: C, 47.8; H, 3.3; N, 8.6%.

Example 65

4-Bromo-5-allyloxy-1-phenylbenzimidazole by the Method of Scheme 3

A solution of the above 5-phenol (Example 64) (0.92 g, 3.18 mmol) in DMF (4 mL) was added under nitrogen to s stirred suspension of NaH (0.15 g of a 60% dispersion in oil, 3.81 mmol). After 5 minutes, allyl bromide (0.30 mL, 3.50 mmol) was added and the solution was stirred at room temperature for 1 hour and at 50° C. for 30 minutes. After dilution with brine the mixture was extracted with diethyl ether. The ether portion was washed with 2N NaOH and worked up to give Example 65 (1.03 g, 99%). Mp: (EtOAc/ petroleum ether) 95–96° C.

$^1$H NMR (CDCl$_3$) δ8.15 (s, 1 H, H-2), 7.60–7.56 (m, 2 H, Ph), 7.50–7.46 (m, 3 H, Ph), 7.38 (d, J=8.8 Hz, 1 H, H-7), 7.02 (d, J=8.8 Hz, 1 H, H-6), 6.16–6.09 (m, 1 H, =CH), 5.16–5.47 (m, 1 H, =CHH), 5.32–5.29 (m, 1 H, =CHH), 4.69–4.67 (m, 2 H, OCH$_2$).

$^{13}$C NMR δ151.86 (s), 143.94 (s), 143.23 (d), 135.99 (s), 133.16 (d), 130.13 (d), 129.35 (s), 128.34 (d), 124.00 (d), 117.81 (t), 112.91 (d), 109.39 (d), 103.77 (s), 71.82 (t).

Analysis calculated for C$_{16}$H$_{13}$BrN$_2$O requires: C, 58.4; H, 4.0; N, 8.5%.

Found: C, 58.4; H, 4.0; N, 8.7%.

Example 66

5-(Methylthio)-1-phenylbenzimidazole Hydrochloride by the Method of Scheme 3

A solution of 5-hydroxy-1-phenylbenzimidazole (Example 14) (0.88 g, 4.10 mmol) in 1:1 THF/DMF (15 mL) was added dropwise under nitrogen to a stirred suspension of NaH (0.24 g of a 50% dispersion in oil, 5.00 mmol) in THF (10 mL). After 10 minutes a solution of dimethylthiocarbamyl chloride (0.57 g, 4.6 mmol) in THF (5 mL) was added and the solution was warmed at 60° C. for 1 hour. The cooled solution was partitioned between ether and 2N KOH and the organic portion was worked up and chromatographed on silica. Elution with EtOAc/petroleum ether (7:3) gave the O-benzimidazolyl dimethylthiocarbamate (0.76 g, 65%), mp (EtOAc/petroleum ether) 173–174.5° C.

$^1$H NMR [(CD$_3$)$_2$SO]: d 8.61 (s, 1H, H-2), 7.72–7.62 (m, 4H, Ph), 7.60 (d, J=8.7 Hz, 1H, H-7), 7.54–7.49 (m, 1H, Ph), 7.45 (d, J=2.2 Hz, 1H, H-4), 7.04 (dd, J=8.7, 2.2 Hz, 1H, H-6), 3.39, 3.36 (2s, each 3H, NMe$_2$).

$^{13}$C NMR: 187.03 (s), 149.51 (s), 144.27 (d), 143.78 (s), 135.74 (s), 130.78 (s), 130.03 (d), 127.79 (d), 123.60 (d), 119.02 (d), 113.55 (d), 110.32 (d), 42.80 (q), 38.41 (q).

A solution of this thiocarbamate (0.40 g, 1.40 mmol) in dry sulfolane (20 mL) was refluxed under nitrogen for 5 hours. The cooled solution was poured into brine, extracted with EtOAc and worked up to give an oil which was chromatographed on silica. EtOAc/petroleum ether (1:1) eluted residual sulfolane while EtOAc gave the S-benzimidazolyl dimethylthiocarbamate (0.36 g, 90%) as an oil which was hydrolysed directly. A solution of this crude thiocarbamate (0.36 g, 1.26 mmol) in MeOH (50 mL) and 6 N KOH (5 mL) was refluxed for 6 hours. After removal of the MeOH in vacuo the residue was partitioned between ether and water. The aqueous portion was carefully neutralised with conc. HCl, extracted with EtOAc and the extract worked up to give an oil which was chromatographed on silica. EtOAc eluted 5-mercapto-1-phenylbenzimidazole as an unstable oil (0.16 g, 56%). HCl salt: mp (MeOH/Et$_2$O) 180–184° C.

$^1$NMR (D$_2$O): d 9.44 (s, 1H, H-2), 7.84 (d, J=2.0 Hz, 1H, H-4), 7.75–7.65 (m, 5H, Ph), 7.63 (d, J=8.7 Hz, 1H, H-7), 7.54 (dd, J=8.7, 2.0 Hz, 1H, H-6).

$^{13}$C NMR: 142.48 (d), 135.70 (s), 134.18 (s), 133.94 (s), 133.48 (d), 133.16 (d), 133.12 (s), 130.86 (d), 127.52 (d), 116.70 (d), 116.42 (d).

A solution of the mercaptobenzimidazole (0.14 g, 0.61 mmol) in 1:1 THF/DMF (5 mL) was added dropwise under nitrogen to a stirred suspension of NaH (35 mg of a 50% dispersion in oil, 0.73 mmol). After 5 minutes methyl iodide (42 mL, 0.67 mmol) was added and the solution was stirred at 20° C. for 3 hours, then poured into 1 N NaOH and extracted with ether. The extract was chromatographed on silica, eluting with EtOAc/petroleum ether (1:1) to give Example 66 as an oil (0.09 g, 61%). HCl salt: mp (MeOH/Et$_2$O) 192–195° C.

$^1$NMR (D$_2$O): d 9.45 (s, 1H, H-2), 7.76–7.72 (m, 3H, Ph), 7.67–7.63 (m, 3H, Ph and H-4), 7.57 (d, J=8.9 Hz, 1H, H-7), 7.43 (dd, J=8.9, 1.6 Hz, 1H, H-6), 2.59 (s, 3H, SCH$_3$).

$^{13}$C NMR: 142.09 (d), 141.36 (s), 135.63 (s), 134.18 (s), 133.41 (d), 133.17 (d), 131.55(s), 128.46(d), 127.16(d), 115.91 (d), 113.36(d), 17.57(q).

Purification of Tyrosine Kinases
Epidermal Growth Factor Receptor (EGFr)

Human EGF receptor tyrosine kinase is isolated from A431 human epidermoid carcinoma cells by the following method. Cells were grown in roller bottles in 50% Dulbecco's Modified Eagle medium and 50% HAM F-12 nutrient media (Gibco) containing 10% fetal calf serum. Approximately 10$^9$ cells are lysed in two volumes of buffer containing 20 mM 2-(4N-[2-hydroxymethyl]piperazin-1-yl) ethanesulfonic acid (Hepes), pH 7.4, 5 mM ethylene glycol bis(2-aminoethyl ether) N,N,N',N'-tetraacetic acid (EGTA), 1% Triton X-100, 10% glycerol, 0.1 mM sodium orthovanadate, 5 mM sodium fluoride, 4 mM pyrophosphate, 4 mM benzamide, 1 mM dithiothreitol (DTT), 80 µg/mL aprotinin, 40 µg/mL leupeptin, and 1 mM phenylmethylsulfonyl fluoride (PMSF). After centrifugation at 25,000 xg for 10 minutes, the supernatant is applied to a fast Q sepharose column (Pharmacia) and eluted with a linear gradient from 0.1 M NaCl to 0.4 M NaCl in 50 mM Hepes, 10% glycerol, pH 7.4. Enzyme active fractions are pooled, divided into aliquots and stored at −100° C.

Platelet Derived Growth Factor Receptor (PDGFr) and Fibroblast Growth Factor Receptor (FGFr)

Full length cDNAs for the mouse PDGF-β and human FGF-1 (flg) receptor tyrosine kinases were obtained from J. Escobedo and are prepared as described in *J. Biol. Chem.*, 262: 1482–1487 (1991). PCR primers are designed to amplify a fragment of DNA that codes for the intracellular tyrosine kinase domain. The fragment is melded into a baculovirus vector, cotransfected with AcMNPV DNA, and the recombinant virus isolated. SF9 insect cells are infected with the virus to overexpress the protein, and the cell lysate is used for the assay.

Other Kinases c-Src kinase is purified from baculovirus infected insect cell lysates using an antipeptide monoclonal antibody directed against the N-terminal 2–17 amino acids as described previously by Fry, et al, *Anticancer Drug Design*. 9: 331–351 (1994). Protein kinase C (PKC) is obtained as a rat brain preparation from Promega.

Kinase Assays
EGFr

Enzyme assays for IC$_{50}$ determinations are performed in 96-well filter plates (Millipore MADVN6550). The total volume is 0.1 mL containing 20 mM Hepes, pH 7.4, 50 µM sodium vanadate, 40 mM magnesium chloride, 10 µM ATP containing 0.5 µCi of [$^{32}$P]ATP, 20 µg of polyglutamic acid/tyrosine (Sigma Chemical Co, St. Louis, Mo.), 10 ng of EGF receptor tyrosine kinase and appropriate dilutions of inhibitor. All components except the ATP are added to the well and the plate is incubated with shaking for 10 minutes at 25° C. The reaction is started by adding [$^{32}$P]ATP and the plate is incubated at 25° C. for 10 minutes. The reaction is terminated by addition of 0.1 mL of 20% trichloroacetic acid (TCA). The plate is kept at 4° C. for at least 15 minutes to allow the substrate to precipitate. The wells are then washed 5 times with 0.2 mL of 10% TCA, and $^{32}$p incorporation is determined with a Wallac beta plate counter.

PDGFr and FGFr

The assay is performed in 96-well plates (100 µL/incubation/well), and conditions are optimized to measure the incorporation of $^{32}$p from [γ$^{32}$P]-ATP into a glutamate-tyrosine copolymer substrate. Briefly, to each well is added 82.5 µL of incubation buffer containing 25 mM Hepes (pH 7.0), 150 mM NaCl, 0.1% Triton X-100, 0.2 mM PMSF, 0.2 mM sodium vanadate, 10 mM manganese chloride, and 750 µg/mL of poly (4:1) glutamate-tyrosine followed by 2.5 µL of inhibitor and 5 µL of enzyme lysate (7.5 µg/µL FGFR-TK or 6.0 µg/µL PDGFR-TK) to initiate the reaction. Following a 10 minute incubation at 25° C., 10 µL of [γ$^{32}$P]-ATP (0.4 µCi plus 50 µM ATP) is added to each well and samples are incubated for an additional 10 minutes at 25° C. The reaction is terminated by the addition of 100 µL of 30% trichloroacetic acid (TCA) containing 20 mM sodium pyrophosphate and precipitation of material onto glass fiber filter mats (Wallac). Filters are washed 3 times with 15% TCA containing 100 mM sodium pyrophosphate and the radioactivity retained on the filters counted in a Wallac 1250 Betaplate reader. Nonspecific activity is defined as radioactivity retained on the filters following incubation of samples with buffer alone (no enzyme). Specific enzymatic activity is defined as total activity (enzyme plus buffer) minus nonspecific activity. The concentration of a compound that inhibited specific activity by 50% ($IC_{50}$) is determined based on the inhibition curve.

c-Src

The antibody, covalently linked to 0.65-μm latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 μg/mL each of leupeptin, pepstatin, and aprotinin. Insect cell lysate containing the c-Src protein is incubated with these beads for 3 to 4 hours at 4° C. with rotation. At the end of the lysate incubation, the beads are rinsed 3 times in lysis buffer, resuspended in lysis buffer containing 10% glycerol, and frozen. These latex beads are thawed, rinsed 3 times in assay buffer which is comprised of 40 mM tris pH 7.5, 5 mM magnesium chloride, and suspended in the same buffer. In a Millipore 96-well plate with a 0.65 μm polyvinylidine membrane bottom are added the reaction components: 10-μL c-Src beads, 10 μL of 2.5 mg/mL poly glutamate-tyrosine substrate, 5 μM ATP containing 0.2 μCi labeled $^{32}$P-ATP, 5 μL DMSO containing inhibitors or as a solvent control, and buffer to make the final volume 125 μL. The reaction is started at room temperature by addition of the ATP and quenched 10 minutes later by the addition of 125 μL of 30% TCA, 0.1 M sodium pyrophosphate for 15 minutes on ice. The plate is then filtered and the wells washed with two 250-μL aliquots of 15% TCA, 0.1 M pyrophosphate. The filters are punched, counted in a liquid scintillation counter, and the data examined for inhibitory activity in comparison to a known inhibitor such as erbstatin. The method is described more fully in *J. Med. Chem.*, 37: 598–609 (1994).

Cascade Assay for Inhibitors of the MAP Kinase Pathway (APK Assay)

Incorporation of $^{32}$P into myelin basic protein (MBP) is assayed in the presence of a glutathione S-transferase fusion protein containing p44MAP kinase (GST-MAPK) and a glutathione S-transferase fusion protein containing p45MEK (GST-MEK). The assay solution contains 20 mM HEPES, pH 7.4, 10 mM magnesium chloride, 1 mM manganese chloride, 1 mM EGTA, 50 μM [$\gamma^{32}$P]ATP, 10 μg GST-MEK, 0.5 μg GST-MAPK and 40 μg MBP in a final volume of 100 μL. Reactions are stopped after 20 minutes by addition of trichloroacetic acid and filtered through a GF/C filter mat. $^{32}$P retained on the filter mat is determined using a 1205 betaplate. Compounds are assessed at 10 μM for ability to inhibit incorporation of $^{32}$P.

To ascertain whether compounds are inhibiting GST-MEK or GST MAPK, two additional protocols are employed. In the first protocol, compounds are added to tubes containing GST MEK, followed by addition of GST-MAPK, MBP and [$\gamma^{32}$P]ATP. In the second protocol, compounds are added to tubes containing both GST-MEK and GST-MAPK, followed by MBP and [$\gamma^{32}$P]ATP. Compounds that show activity in both protocols are scored as MAPK inhibitors, while compounds showing activity in only the first protocol are scored as MEK inhibitors.

Other Kinases

An assay using the intracellular kinase domains of insulin receptor (INSr) is performed as described for the EGF receptor except that 10 mM manganese chloride is included in the reaction. The PKC assay is performed as previously described by Martiny-Baron, et al., *J. Biol. Chem.* 268: 9194–9197 (1993).

Table 1 provides inhibition data against receptor kinases for compounds of the present invention.

TABLE 1

| Example Number | PDGF $IC_{50}$ (μM) | FGF $IC_{50}$ (μM) | c-Src $IC_{50}$ (μM) | EGFr $IC_{50}$ (μM) | INSr $IC_{50}$ (μM) | APK $IC_{50}$ (μM) | PKC $IC_{50}$ (μM) |
|---|---|---|---|---|---|---|---|
| 1 | 9.3 | >50 | >50 | >50 | >50 | ND | ND |
| 2 | 3.8 | 50 | >50 | ND | >50 | ND | ND |
| 3 | 3.6 | >50 | >50 | >50 | >50 | ND | ND |
| 4 | 6.8 | >50 | >50 | ND | >50 | ND | ND |
| 5 | 12 | >50 | >50 | ND | >50 | ND | ND |
| 6 | 1.8 | 5.8 | >50 | ND | >50 | ND | ND |
| 7 | 7.2 | >50 | >50 | >50 | >50 | ND | ND |
| 8 | 5.6 | >50 | ND | ND | ND | ND | ND |
| 9 | 13.5 | >50 | >50 | ND | ND | ND | ND |
| 10 | 12.3 | 50 | >50 | ND | >50 | ND | ND |
| 11 | 10.6 | >50 | >50 | >50 | >50 | ND | ND |
| 12 | 4.4 | >50 | >50 | 50 | >50 | ND | ND |
| 13 | 0.4 | 22 | >50 | <50 | >50 | 5 | >50 |
| 14 | 0.4 | 6.4 | >50 | >50 | >50 | ND | ND |
| 15 | 4.0 | 51 | ND | ND | ND | ND | ND |
| 16 | 9.3 | 28 | 50 | >50 | >50 | ND | ND |
| 17 | 0.8 | 6.6 | >50 | >50 | >50 | ND | ND |
| 18 | 1.6 | 9.9 | <50 | >50 | >50 | ND | ND |
| 19 | 2.7 | 36 | >50 | >50 | >50 | ND | ND |
| 20 | 0.9 | 14 | ND | ND | ND | ND | ND |
| 21 | 8.4 | 50 | 50 | <50 | >50 | ND | ND |
| 22 | 10 | 49 | >50 | ND | >50 | ND | ND |
| 23 | 3.3 | 32 | <50 | ND | >50 | ND | ND |
| 24 | 2.4 | 41 | >50 | ND | >50 | ND | ND |
| 25 | 5.3 | 37 | >50 | ND | ND | ND | ND |
| 26 | 11.7 | >50 | >50 | <50 | >50 | ND | ND |
| 27 | 1.8 | 26 | >50 | >50 | >50 | ND | ND |
| 28 | 0.2 | 26 | >50 | ND | >50 | ND | ND |
| 29 | 0.3 | 35 | >50 | ND | >50 | ND | ND |
| 30 | <50 | 50 | >50 | ND | >50 | ND | ND |
| 31 | 1.4 | >50 | >50 | ND | >50 | ND | ND |
| 32 | 0.6 | 35 | >50 | ND | >50 | ND | ND |
| 33 | 0.3 | 15 | >50 | ND | ND | ND | ND |
| 34 | 0.3 | 18 | 50 | ND | ND | ND | ND |
| 35 | 0.7 | 27 | <50 | ND | >50 | ND | ND |
| 36 | 1.5 | 45 | 29 | ND | >50 | ND | ND |
| 37 | 0.2 | 4.1 | 14 | >40 | >50 | 27 | >50 |
| 38 | 0.7 | 28 | >50 | >40 | >50 | 45 | >50 |
| 39 | 0.2 | 9.8 | >50 | >40 | >50 | 18 | >50 |
| 40 | 6.4 | >50 | ND | ND | ND | ND | ND |
| 41 | 2.1 | >50 | >50 | >50 | <50 | ND | ND |
| 42 | 5.4 | >50 | ND | ND | ND | ND | ND |
| 43 | 13 | >50 | >50 | >50 | >50 | ND | ND |
| 44 | 9.6 | >50 | ND | ND | ND | ND | ND |
| 45 | 0.3 | 18 | >50 | <40 | >50 | 37 | >50 |
| 46 | 1.2 | 25 | 40 | ND | >50 | ND | ND |
| 47 | 2.3 | 11 | >50 | ND | >50 | ND | ND |
| 48 | 2.2 | 27 | >50 | ND | >50 | ND | ND |
| 49 | 1.0 | >50 | >50 | ND | >50 | ND | ND |
| 50 | 2.5 | >50 | >50 | ND | >50 | ND | ND |
| 51 | 0.9 | 50 | 33 | ND | >50 | ND | ND |
| 52 | 4.3 | 22 | 34 | ND | ND | ND | ND |
| 53 | 0.4 | 12 | 50 | ND | >50 | ND | ND |
| 54 | 1.1 | 25 | >50 | ND | >50 | ND | ND |
| 55 | 2.5 | 5.3 | >50 | ND | >50 | ND | ND |
| 56 | 0.7 | 6.5 | >50 | ND | ND | ND | ND |
| 57 | 0.5 | 25 | >50 | ND | ND | ND | ND |
| 58 | 0.2 | 6 | 50 | ND | ND | ND | ND |
| 59 | 0.3 | 12 | 25 | ND | ND | ND | ND |
| 60 | >50 | >50 | >50 | ND | ND | ND | ND |
| 61 | 25 | 1.9 | 0.5 | ND | ND | ND | ND |
| 62 | 50 | 50 | >50 | ND | ND | ND | ND |
| 63 | <50 | >50 | 40 | ND | ND | ND | ND |
| 64 | >50 | >50 | >50 | ND | ND | ND | ND |
| 65 | >50 | >50 | >50 | ND | ND | ND | ND |

ND = Not determined.

Cell Culture

PDGF Receptor Autophosphorylation Assay

Rat aorta smooth muscle cells (RASMC) are isolated from the thoracic aorta of rats and explanted according to the method of Ross, *J. Cell. Biol.*, 30: 172–186 (1971). Cells are grown in Dulbecco's modified Eagle's medium (DMEM, Gibco) containing 10% fetal calf serum (FBS, Hyclone, Logan, Utah), 1% glutamine (Gibco) and 1% penicillin/ streptomycin (Gibco). Cells are identified as smooth muscle cells by their "hill and valley" growth pattern and by fluorescent staining with a monoclonal antibody specific for SMC $\mu$-actin (Sigma). RASMC are used between passages 5 and 20 for all experiments. Test compounds are prepared in dimethylsulfoxide (DMSO) in order to achieve consistency in the vehicle and to ensure compound solubility. Appropriate DMSO controls are simultaneously evaluated with the test compounds.

Rat aortic smooth muscle cells are grown to confluencey in 100 mm dishes. Growth medium is removed and replaced with serum-free medium and cells are incubated at 37° C. for an additional 24 hours. Test compounds are then added directly to the medium and cells incubated for an additional 2 hours. After 2 hours PDGF-BB is added at a final concentration of 30 ng/mL for 5 minutes at 37° C. to stimulate autophosphorylation of PDGF receptors. Following growth factor treatment, the medium is removed, and cells are washed with cold phosphate-buffered saline and immediately lysed with 1 mL of lysis buffer (50 mM Hepes, pH 7.5, 150 mM NaCl, 10% glycerol, 1% Triton-X 100, 1 mM EDTA, 1 mM EGTA, 50 mM NaF, 1 mM sodium orthovanadate, 30 mM p-nitrophenyl phosphate, 10 mM sodium pyrophosphate, 1 mM phenylmethyl sulfonyl fluoride, 10 $\mu$g/mL aprotinin and 10 $\mu$g/mL leupeptin). Lysates are centrifuged at 10,000 xg for 10 minutes. Supernatants are incubated with 10 $\mu$L of rabbit anti human PDGF type AB receptor antibody (1:1000) for 2 hours. Following the incubation, protein-A-sepharose beads are added for 2 hours with continuous mixing, and immune complexes bound to the beads washed 4 times with 1 mL lysis wash buffer. Immune complexes are solubilized in 40 $\mu$L of Laemmli sample buffer and electrophoresed in 8–16% SDS polyacrylamide gels. Following electrophoresis, separated proteins are transferred to nitrocellulose and immunoblotted with a 1:1000 dilution of antiphosphotyrosine monoclonal antibody (UBI clone 4G10; #05-321). Following extensive washing with PBS-0.2% tween-20, the blots are incubated with horseradish peroxidase labeled goat antimouse IgG (1:5000; Bio-Rad Inc, Hercules, Calif.) and protein levels are detected by enhanced chemiluminescence (ECL) detection system according to the instructions of the supplier (Amersham Inc, Arlington Heights, Ill.). The density of the protein bands are determined using NIH Image software (v. 1.56) and $IC_{50}$ values are generated from the densitometric data.

Table 2 provides data for inhibition of PDGF-stimulated receptor autophospharylation in rat aorta smooth muscle cells.

TABLE 2

| Example Number | $IC_{50}$ ($\mu$M) |
|---|---|
| 8 | >10 |
| 11 | >10 |
| 13 | 2 |
| 38 | 0.7 |
| 40 | >10 |
| 45 | 3.5 |
| 59 | 2.2 |

Human Colon Carcinoma Growth Delay Assay

Human colon carcinoma cells are seeded into 96-well tissue culture plates in a final volume of 180 $\mu$L of 10% fetal bovine serum containing growth media and allowed to incubate overnight (37° C., 5% $CO_2$, 95% air). Cells of the SW620 cell line are seeded at 1.0–1.5×10$^4$ cells per well. Cells of the HCT8 and HT29 cell lines are seeded at 2–4×10$^3$ cells per well. Serially diluted drug solutions are prepared in growth medium at 10 xconcentration; 20 $\mu$L of these solutions are added to duplicate wells and incubated with the cells for 3 days in a cell culture incubator. At the end of the incubation period, cells are fixed with 100 $\mu$L per well of 10% trichloroacetic acid after removing the drug/culture medium. The plates are washed 5 times with tap water and stained with 100 $\mu$L per well of 0.075% sulforhodamine B in 1% acetic acid for 10 minutes. The plates are rinsed 4 times and allowed to air dry. The stain in the wells are solubilized by the addition of 10 mM unbuffered Tris base and the absorbance read using a microtiter plate optical reader. Inhibition of cell growth is calculated from absorbance data of the treated cells compared to untreated control cells.

Human Colon Carcinoma Clonogenic Assay

Human colon carcinoma cells are seeded into 6 well plates in volumes of 3 mL and allowed to incubate overnight (37° C., 5% $CO_2$, 95% air). SW620 cells are seeded at 7×10$^5$ per well; HCT8 cells are seeded at 5×10$^5$ per well; HT29 cells are seeded at 4×10$^5$ cells per well. Serially diluted drugs are prepared at 200 xthe final concentration and 15 $\mu$L are added to each of duplicate wells. Cells are incubated with drug for 2 days, rinsed once with 1 mL of trypsin+ EDTA, and then trypsinized with the same trypsin solution. After trituration and centrifugation at 750 xg for 3 minutes, the cells are suspended in serum-free growth medium and counted using an electronic particle counter. An agarose mixture appropriate for the cloning of each cell line is made using 10% fetal bovine serum in growth medium (SW620-0.35% agarose, HCT8 and HT29-0.4% agarose). An appropriate volume of medium containing the drug treated cells is suspended into the agarose-serum mixture to give final cell concentrations in 2.5 mL of 1.75×10$^4$ SW620, 1.25×10$^4$ HCT8, and 7.5×10$^3$ HT29. One milliliter of each of these cell suspensions is added to duplicate wells of 6 well plates previously prepared with 10% serum/growth medium/ 1% agarose plugs. The cells in these plates are incubated for approximately 2 weeks in the incubator and stained with 1 mL per well of 1 mg/mL iodonitrotetrazolium violet stain. The visible colonies are counted with an electronic optical colony counter and the clonogenicity of treated cells calculated in comparison to untreated control cells.

Table 3 provides data for inhibition of growth in human adenocarcinoma cell lines.

TABLE 3

| Example Number | Cell Line (IC$_{50}$, μM) | | | | | |
|---|---|---|---|---|---|---|
| | HCT-8 Growth Delay | SW-620 Growth Delay | HT-29 Growth Delay | HCT-8 Clonogenic | SW-620 Clonogenic | HT-29 Clonogenic |
| 11 | ND | >25 | ND | ND | 2.1, >5 | ND |
| 13 | ND | >25 | ND | ND | >5 | ND |
| 59 | ND | >25 | ND | ND | >25 | ND |

ND = Not determined.

What is claimed is:

1. A method of treating protein tyrosine kinase mediated cancer, the method comprising administering to a patient having protein tyrosine kinase mediated cancer a therapeutically effective amount of a compound of Formula I

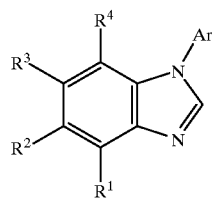

wherein

Ar is aryl, or substituted aryl;

$R^1$, $R^2$, $R^3$, and $R^4$ are each independently hydrogen, $C_1$–$C_6$ alkyl, —$OC_1$–$C_6$ alkyl, —OH, halogen, —$CO_2R^4$, —$CONR^aR^b$, —$NO_2$, —$NR^aR^b$, —$COC_1$–$C_6$ alkyl, —CHO, —CN, —$SO_2C_1$–$C_6$ alkyl,

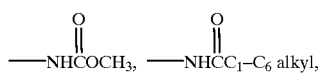

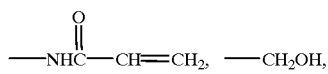

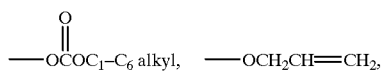

—$OCH_2$—$CH(OH)CH_2OH$, —$O(CH_2)_nNR^aR^b$, —SH,

—$SC_1$–$C_6$ alkyl, or —$S(CH_2)_n$—$NR^aR^b$, or $R^2$ and $R^3$ together can form a cycloalkyl ring and $R^a$ and $R^b$ are each independently hydrogen or $C_1$–$C_6$ alkyl, n is 0 to 5, or a pharmaceutically acceptable salt, ester, amide, or prodrug thereof.

2. A method of treating or preventing restenosis, the method comprising administering to a patient having restenosis or at risk of having restenosis a therapeutically effective amount of a compound of Formula I

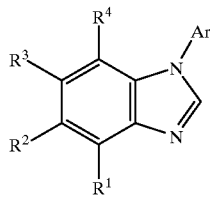

wherein

Ar is aryl, or substituted phenyl wherein the phenyl substituent is halogen, $C_1$–$C_8$ alkyl, —CN, —$CF_3$, —$NO_2$, —$NH_2$—$NHC_1$–$C_8$ alkyl, —$N(C_1$–$C_8$ alkyl)$_7$, —$OC_1$–$C_8$alkyl, or —OH $R^1$, $R^2$, $R^3$, and $R^4$ are each independently hydrogen, $C_1$–$C_6$ alkyl, —$OC_1$–$C_6$ alkyl, —OH, halogen, —$CO_2R^2$, —$CONR^aR^b$, —$NO_2$, —$NR^aR^b$, —$COC_1$–$C_6$ alkyl, —CHO, —CN, —$SO_2C_1$–$C_6$ alkyl,

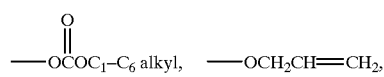

—$OCH_2CH(OH)CH_2OH$, —$O(CH_2)_nNR^aR^b$, —SH, —$SC_1$–$C_6$ alkyl, or —$S(CH_2)_n$—$NR^aR^b$, or $R^2$ and $R^3$ together can form a cycloalkyl ring; and $R^a$ and $R^b$ are each independently hydrogen or $C_1$–$C_6$ alkyl, n is 0 to 5, or a pharmaceutically acceptable salt, ester, amide, or prodrug thereof.

3. A method of treating atherosclerosis, the method comprising administering to a patient having atherosclerosis a therapeutically effective amount of a compound of Formula I

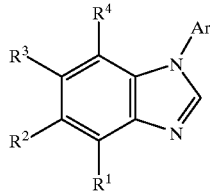

wherein

Ar is aryl, or substituted phenyl wherein the phenyl substituent is halogen, $C_1$–$C_8$alkyl, —CN, —$CF_3$, —$NO_2$, —$NH_2$—$NHC_1$–$C_8$alkyl, —$N(C_1$–$C_8$alkyl)$_2$, —$OC_1$–$C_8$alkyl, or —OH $R^1$, $R^2$, $R^3$, and $R^4$ are each independently hydrogen, $C_1-C_6$ alkyl, $-OC_1-C_6$ alkyl, $-OH$, halogen, $-CO_2R^a$, $-CONR^aR^b$, $-NO_2$, $-NR^aR^b$, $-COC_1-C_6$ alkyl, $-CHO$, $-CN$, $-SO_2C_1-C_6$ alkyl,

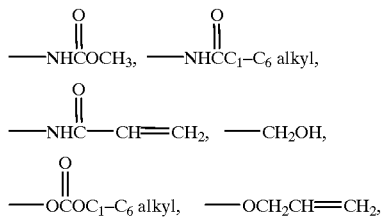

$-OCH_2CH(OH)CH_2OH$, $-O(CH_2)_nNR^aR^b$, $-SH$, $-SC_1-C_6$ alkyl, or $-S(CH_2)_n-NR^aR^b$, or $R^2$ and $R^3$ together can form a cycloalkyl ring; and $R^a$ and $R^b$ are each independently hydrogen or $C_1-C_6$ alkyl, n is 0 to 5, or a pharmaceutically acceptable salt, ester, amide, or prodrug thereof.

4. A method of treating psoriasis, the method comprising administering to a patient having psoriasis a therapeutically effective amount of a compound of Formula I

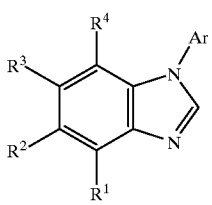

wherein

Ar is aryl, or substituted aryl;

$R^1$, $R^2$, $R^3$, and $R^4$ are each independently hydrogen, $C_1-C_6$ alkyl, $-OC_1-C_6$ alkyl, $-OH$, halogen, $-CO_2R^a$, $-CONR^aR^b$, $-NO_2$, $-NR^aR^b$, $-COC_1-C_6$ alkyl, $-CHO$, $-CN$, $-SO_2C_1-C_6$ alkyl,

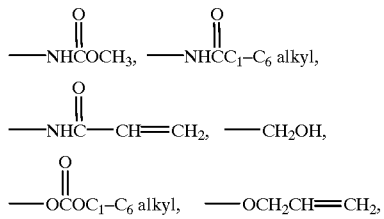

$-OCH_2CH(OH)CH_2OH$, $-O(CH_2)_nNR^aR^b$, $-SH$, $-SC_1-C_6$ alkyl, or $-S(CH_2)_n-NR^aR^b$, or $R^2$ and $R^3$ together can form a cycloalkyl ring; and $R^a$ and $R^b$ are each independently hydrogen or $C_1-C_6$ alkyl, n is 0 to 5, or a pharmaceutically acceptable salt, ester, amide, or prodrug thereof.

5. A method of inhibiting protein tyrosine kinases, the method comprising administering to a patient in need of protein tyrosine kinases inhibition a protein tyrosine kinase inhibiting amount of a compound of Formula I

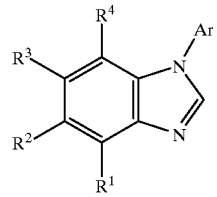

wherein

Ar is aryl, or substitued aryl, heteroaryl;

$R^1$, $R^2$, $R^3$, and $R^4$ are each independently hydrogen, $C_1-C_6$ alkyl, $-OC_1-C_6$ alkyl, $-OH$, halogen, $-CO_2R^a$, $-CONR^aR^b{}^2$, $-NO_2$, $-NR^aR^b$, $-COC_1-C_6$ alkyl, $-CHO$, $-CN$, $-SO_2C_1-C_6$ alkyl,

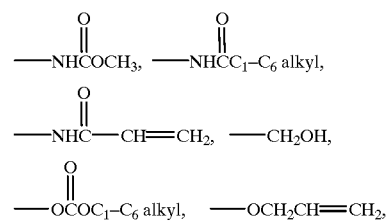

$-OCH_2CH(OH)CH_2OH$, $-O(CH_2)_nNR^aR^b$, $-SH$, $-SC_1-C_6$ alkyl, or $-S(CH_2)_n-NR^aR^b$, or $R^2$ and $R^3$ together can form a cycloalkyl ring; and $R^a$ and $R^b$ are each independently hydrogen or $C_1-C_6$ alkyl, n is 0 to 5, or a pharmaceutically acceptable salt, ester, amide, or prodrug thereof.

6. The method of claim 5 wherein the protein tyrosine kinase is FGFr.

7. The method of claim 5 wherein the protein tyrosine kinase is PDGFr.

8. A method of treating or preventing restenosis, the method comprising administering to a patient having restenosis or at risk of having restenosis a therapeutically effective amount of the compound 1-(3-formlphenyl) benzimidazole or a pharmaceutically acceptable salt, ester, amide, or prodrug thereof.

9. A method of treating atherosclerosis, the method comprising administering to a patient having atherosclerosis a therapeutically effective amount of the compound 1-(3-formlphenyl)benzimidazole or a pharmaceutically acceptable salt, ester, amide or prodrug thereof.

\* \* \* \* \*

UNITED STATES PATENT AND TRADEMARK OFFICE
CERTIFICATE OF CORRECTION

PATENT NO. : 5,990,146
DATED : Nov. 23, 1999
INVENTOR(S) : Boschelli et al.

It is certified that error appears in the above-identified patent and that said Letters Patent is hereby corrected as shown below:

Column 45, line 40, "$-CO_2R^4$" should read "$-CO_2R^a$".

Column 45, line 56, "$-OCH_2-CH(OH)CH_2OH,$" should read "$-OCH_2CH(OH)CH_2OH,$".

Column 46, line 27, "$-NH_2$" should read "$-NH_2,$".

Column 46, line 27, "$-N(C_1-C_8\ alkyl)_7$" should read "$-N(C_1-C_8\ alkyl)_2$".

Column 46, line 31, "$-CO_2R^2$" should read "$-CO_2R^a$".

Column 46, line 66, "$-NH_2$" should read "$-NH_2,$".

Column 47, line 38, "$-CO_2R^2$" should read "$-CO_2R^a$".

Column 48, line 20, "$-CONR^aR^{b\ 2},$" should read "$-CONR^aR^b,$".

Signed and Sealed this

Eighteenth Day of July, 2000

Attest:

Q. TODD DICKINSON

*Attesting Officer*     *Director of Patents and Trademarks*